(12) United States Patent
van den Bogerd et al.

(10) Patent No.: US 8,900,693 B2
(45) Date of Patent: Dec. 2, 2014

(54) POLYCARBONATE COMPOSITIONS HAVING INFRARED ABSORBANCE, METHOD OF MANUFACTURE, AND ARTICLES PREPARED THEREFROM

(75) Inventors: Jos A van den Bogerd, St. Annaland (NL); Josephus Hubertus Cornelius Maria Dekkers, Breda (NL); Rein Mollerus Faber, Bergen op Zoom (NL); Jan-Willem Goedmakers, Putte (NL); Christianus Johannes Jacobus Maas, Rilland (NL)

(73) Assignee: Sabic Global Technologies B.V. (NL)

( * ) Notice: Subject to any disclaimer, the term of this patent is extended or adjusted under 35 U.S.C. 154(b) by 0 days.

(21) Appl. No.: 11/180,746

(22) Filed: Jul. 13, 2005

(65) Prior Publication Data

US 2007/0015081 A1 Jan. 18, 2007

(51) Int. Cl.
*B32B 27/32* (2006.01)
*B32B 5/16* (2006.01)
*B32B 17/10* (2006.01)

(52) U.S. Cl.
USPC ............ 428/220; 428/323; 428/328; 428/339

(58) Field of Classification Search
USPC ........................................................ 430/270.1
See application file for complete search history.

(56) References Cited

U.S. PATENT DOCUMENTS

| | | | |
|---|---|---|---|
| 3,657,057 A | 4/1972 | Shorr et al. | |
| 3,885,855 A | 5/1975 | Gross | 350/1 |
| 4,031,063 A | 6/1977 | Conciatori et al. | |
| 4,250,078 A | 2/1981 | McFarlane et al. | |
| 4,323,668 A | 4/1982 | Brunelle | 528/173 |
| 4,648,710 A | 3/1987 | Ban et al. | |
| 4,686,791 A | 8/1987 | Miyata | |
| 4,804,692 A | 2/1989 | Lundy et al. | |
| 4,895,904 A | 1/1990 | Allingham | 523/135 |
| 5,103,336 A | 4/1992 | Sieloff | |
| 5,118,748 A * | 6/1992 | Fujita et al. | 524/436 |
| 5,405,680 A | 4/1995 | Chang et al. | 428/212 |
| 5,712,332 A | 1/1998 | Kaieda et al. | |
| 5,834,152 A * | 11/1998 | Yasunaga et al. | 430/122.2 |
| 5,907,026 A | 5/1999 | Factor et al. | |
| 6,022,920 A | 2/2000 | Maxwell et al. | 524/431 |
| 6,060,154 A | 5/2000 | Adachi et al. | 428/323 |

(Continued)

FOREIGN PATENT DOCUMENTS

DE 10392543 T5 4/2005
EP 0 454 349 A2 4/1991

(Continued)

OTHER PUBLICATIONS

European Search Report for EP03258166. Mailed on Mar. 19, 2004.
European Search Report for EP 04257697. Mailed on May 4, 2005.
International Search Report for PCT/US2004/041140. Mailed Apr. 20, 2005.
JP2004-043764. Publication Date Feb. 12, 2004. "Infrared Light-Blocking Fluorine Resin Film". (Abstract Only).

(Continued)

*Primary Examiner* — Amanda C. Walke
(74) *Attorney, Agent, or Firm* — Cantor Colburn LLP

(57) ABSTRACT

A composition is disclosed, comprising a polycarbonate resin, an inorganic infrared shielding additive, and carbon black, wherein an article prepared from the composition has the inorganic infrared shielding additive present at about 0.01 to about 1.0 grams per square meter, and carbon black present at about 0.001 to about 2.0 grams per square meter. The article prepared from the composition meets at least one scale requirement for European Norm EN 169 and/or EN 171, and is useful for preparing infrared shielding protective eyewear with low haze.

19 Claims, 1 Drawing Sheet

(56) References Cited

U.S. PATENT DOCUMENTS

Figure 1:
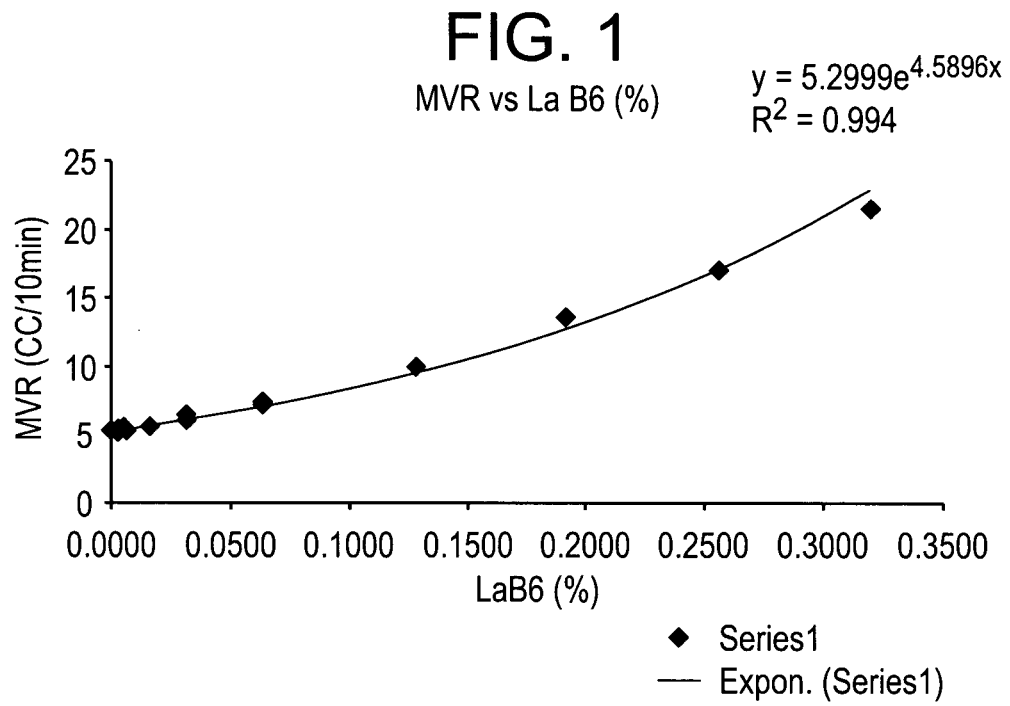

| | | | |
|---|---|---|---|
| 6,063,854 | A | 5/2000 | Naarmann et al. |
| 6,136,441 | A | 10/2000 | MacGregor et al. |
| 6,143,387 | A | 11/2000 | Kubler et al. |
| 6,221,945 | B1 | 4/2001 | Kuno et al. ............... 524/401 |
| 6,265,522 | B1 | 7/2001 | Brunelle et al. |
| 6,270,944 | B1 | 8/2001 | Wolk et al. |
| 6,277,187 | B1 | 8/2001 | Kuno et al. ............ 106/287.16 |
| 6,319,613 | B1 | 11/2001 | Takeda et al. ............... 428/412 |
| 6,420,512 | B1 | 7/2002 | McCloskey et al. |
| 6,482,511 | B1* | 11/2002 | Martinez Antonio ......... 428/364 |
| 6,482,570 | B1 | 11/2002 | Hotta |
| 6,548,623 | B2 | 4/2003 | Brunelle et al. ............ 528/196 |
| 6,630,527 | B2 | 10/2003 | Pierre et al. |
| 6,733,872 | B2 | 5/2004 | Nagai |
| 6,749,939 | B2 | 6/2004 | Desai et al. |
| 6,780,515 | B2 | 8/2004 | Dobler |
| 7,514,523 | B2* | 4/2009 | Chen et al. ................ 528/196 |
| 7,709,184 | B2* | 5/2010 | Teng ........................... 430/302 |
| 2002/0182389 | A1 | 12/2002 | Dobler ......................... 428/212 |
| 2003/0054160 | A1 | 3/2003 | Fisher et al. ................ 428/328 |
| 2003/0072945 | A1 | 4/2003 | Pickett et al. |
| 2003/0094600 | A1 | 5/2003 | Dobler et al. |
| 2003/0175488 | A1* | 9/2003 | Asthana et al. .............. 428/212 |
| 2004/0028920 | A1* | 2/2004 | Fujita et al. ................. 428/458 |
| 2004/0071957 | A1* | 4/2004 | Fujita ........................... 428/328 |
| 2004/0131845 | A1 | 7/2004 | Fujita |
| 2004/0152806 | A1* | 8/2004 | Koga et al. .................. 524/115 |
| 2004/0234778 | A1 | 11/2004 | Fukatani et al. |
| 2005/0095433 | A1 | 5/2005 | Bogerd et al. |
| 2005/0165148 | A1 | 7/2005 | Bogerd et al. |
| 2005/0215750 | A1* | 9/2005 | Koga et al. .................. 528/196 |
| 2006/0251996 | A1* | 11/2006 | Bogerd et al. ............... 430/323 |

FOREIGN PATENT DOCUMENTS

| | | |
|---|---|---|
| EP | 0 727 306 A2 | 1/1996 |
| EP | 0 727 306 B1 | 1/1996 |
| EP | 0 894 620 A1 | 4/1997 |
| EP | 0 905 100 B1 | 9/1998 |
| EP | 0 943 587 A1 | 10/1998 |
| EP | 1 008 564 A1 | 12/1999 |
| EP | WO 02/060988 A1 | 8/2002 |
| EP | WO 02/077081 A1 | 10/2002 |
| EP | 1319683 A1 | 6/2003 |
| EP | 1419999 A1 | 5/2004 |
| EP | 1529632 A1 | 5/2005 |
| EP | 1541012 A1 | 6/2005 |
| EP | 1724110 A1 | 11/2006 |
| GB | 2014513 A | 8/1979 |
| GB | 2057355 A1 | 4/1981 |
| JP | 11181336 A | 7/1999 |
| JP | 2000024591 A | 1/2000 |
| JP | 200096034 | 4/2000 |
| JP | 2000234066 A | 8/2000 |
| JP | 2000319554 A | 11/2000 |
| JP | 2001049190 A | 2/2001 |
| JP | 200189202 A | 4/2001 |
| JP | 2001262061 A | 9/2001 |
| JP | 2001311006 A | 11/2001 |
| JP | 2002369629 A | 12/2002 |
| JP | 2003327717 A | 11/2003 |
| JP | 2006122803 A | 5/2006 |
| JP | 200772484 A | 3/2007 |
| JP | 2008104835 A | 5/2008 |
| JP | 200963117 A | 3/2009 |
| WO | WO9502504 A1 | 1/1995 |
| WO | 9811031 A1 | 3/1998 |
| WO | 02083410 A1 | 10/2002 |
| WO | WO03074270 A2 | 9/2003 |
| WO | WO03095561 A1 | 11/2003 |

OTHER PUBLICATIONS

JP2004-059875. Publication Date: Feb. 26, 2004. "Masterbatch Containing Heat Ray Shielding Ingredient, Heat Ray Shielding Transparent Resin Molding Applied with the Masterbatch and Laminate Thereof". (Abstract Only).

JP06-122803, Publication Date: May 6, 1994. "Rare Earth Element-Containing Resin and its Production". (Abstract Only).

JP07-070356. Publication Date: Mar. 14, 1995. "Resin Composition with Improved Flammability". (Abstract Only).

JP08-104835. Publication Date: Apr. 23, 1996. "Coating Composition and Method of Forming Designed Paint Film". (Abstract Only).

JP09-063117. Publication Date: Mar. 7, 1997. "Optical Information Recording Medium". (Abstract Only).

JP2000-072484. Publication Date: Mar. 7, 2000. "Shielding Material Against Heat Ray, and Coating Liquid and Heat Ray Shielding Film Using That". (Abstract Only).

JP2000-096034. Publication Date: Apr. 4, 2000. Sun Radiation Screening Material, Coating Solution for Sun Radiation Screening Membrane and Sun Radiation Screening Membrane. (Abstract Only).

JP2000-319544. Publication Date: Nov. 21, 2000. Coating Liquid for Forming Heat-Ray and Ultra Violet-Ray Shielding Film, and Heat-Ray and Ultra Violet-Ray Shielding Film Prepared by Using the Liquid. (Abstract Only).

JP2001-089202. Publication Date: Apr. 3, 2001. "Sunlight Shielding Laminated Glass". (Abstract Only).

JP2002-369629. Publication Date: Dec. 24, 2002. "Heat-Insulating Material for Agricultural and Horticultural Facility". (Abstract Only).

JP2003-327717. Publicatoin Date: Nov. 19, 2003. "Heat Ray Shielding Resin Sheet Material and Liquid Additive for Use in Its Manufacture". (Machine Translation).

Schelm, et al. "Dilute LaB6 nanoparticles in polymer as optimized clear solar control glazing". Applied Physics Letters. vol. 82, No. 24. Jun. 16, 2003. pp. 4346-4348.

SMM Sumitomo Metal Mining Brochure "A new IR-active agent to screen out solar heat 'KH'" Sumitomo Metal Mining Co., ltd., Performance Materials Dept., 11-3 Shimbashi, 5-chome, Tokyo 105-8716 Japan—www.smm.co.jp.

SMM Sumitomo Metal Mining Brochure "IR-Shielding Dispersions" Sumitomo Metal Mining Co., ltd., Performance Materials Dept., 11-3 Shimbashi, 5-chome, Tokyo 105-8716 Japan—www.smm.co.jp.

SMM Sumitomo Metal Mining Brochure "Weathering properties of PC sheet incorporated with incorporated KH particles" Jun. 2003.

SMM Sumitomo Metal Mining Co., Ltd. Brochure "Weathering properties of PC sheet incorporated with KH particles" Jan. 2004.

Burkhardt, G. et al. "Plastics, Processing", Ullmann's Encyclopedia of Industrial Chemistry, Wiley-VCH, only posting date Jun. 15, 2000.

BS EN 171:2002 BSI—British Standards Institution. "Personal eye-protection-Infrared filters-transmittance requirements and recommended use". pp. 1-12.

BS EN169:2002. British Standard "Personal eye-protection-Filters for welding and related techniques-Transmittance requirements and recommended use". pp. 1-16.

JP2002369629. Publication Date: Dec. 24, 2002. "Heat-Insulating Material for Agricultural and Horticultural Facility". (Abstract Only).

ISO1133. International Standard. "Plastics-Determination of the melt mass-flow rate (MFR) and the melt volume-flow rate (MVR) of thermoplastics". Jan. 15, 1997 pp. 1-11.

International Search Report for PCT/US2006/025870, International filing date: Jun. 30, 2006, Date of Mailing Jan. 2, 2007, 5 pages.

EP Search Report dated Oct. 11, 2006; European Application No. 05254761.9-1214.

* cited by examiner

MVR vs La B6 (%)

$y = 5.2999e^{4.5896x}$
$R^2 = 0.994$

Haze vs LaB6

POLYCARBONATE COMPOSITIONS HAVING INFRARED ABSORBANCE, METHOD OF MANUFACTURE, AND ARTICLES PREPARED THEREFROM

BACKGROUND OF THE INVENTION

This disclosure relates to polycarbonate compositions, and in particular to polycarbonate compositions having infrared (IR) absorbance, methods of manufacture, and uses thereof.

Polycarbonates are useful for applications in which good impact strength, low haze, and high transparency are desired. On such application for which polycarbonates are suitable is protective eyewear, including that designed to limit ocular exposure to potentially damaging radiation. Included in this category is protective eyewear for applications such as, for example, welding, foundry work, glassblowing, and other similar types of hot work, wherein a range of moderate to high intensity infrared radiation is present. Standards, such as European Norms EN 166, EN 169, and EN 171, have been developed as guidelines for the performance of materials and articles for eyewear for protection from infrared radiation, which block the transmission of an amount of the radiation. Both EN 169, which describes requirements for filters for welding and related techniques, and EN 171, which describes requirements for personal eye protection using infrared filters, include different scales identified by number, that correspond to requirements for acceptable amounts of transmittable radiation. The requirements are to the amounts of infrared radiation, and visible and/or ultraviolet radiation, that are allowable for transmission through the protective eyewear. Protective eyewear can be designed according to these individual scale requirements to provide the user of the eyewear with an acceptable level of exposure for a specific application.

To prepare protective eyewear protection for use in the infrared region, also referred to as the IR region (780 to 2000 nanometers) and that meet these standards, additives that absorb and/or dissipate infrared radiation can be added to polycarbonates. Organic infrared shielding additives derived from polycyclic aromatic amines and salts, such as N,N,N',N'-tetrakis-(p-di-n-butylaminophenyl)-p-phenylenediamine and N,N,N',N'-tetrakis-(p-di-n-butylaminophenyl)-p-benzoquinone-bis-(immonium-hexafluoroantimonate), can provide absorbance in the infrared; however, such compounds generally lack the thermal and oxidative stability needed to withstand extrusion and molding conditions without decomposition.

What is needed therefore, is a polycarbonate composition that meets at least one of the series requirements of one or both of European Norms EN169 and EN171, and is suitable for use in protective eyewear.

A suitable composition desirably is thermally and oxidatively stable, has good impact strength, and suitable level of haze.

SUMMARY OF THE INVENTION

In an embodiment, the above requirements are met by a composition comprising a polycarbonate resin, an inorganic infrared shielding additive, and carbon black, wherein an article prepared from the composition has the inorganic infrared shielding additive present at about 0.01 to about 1.0 grams per square meter, and carbon black present at about 0.001 to about 2.0 grams per square meter. The article so prepared has a haze of less than about 5% as measured at a thickness of about 2.5 mm according to ASTM D1003-00. In another embodiment, an article prepared from the composition has inorganic infrared shielding additive present at about 0.5 to about 8,000 parts per million, and carbon black present at about 1 to about 30,000 parts per million.

In another embodiment, a masterbatch comprises a carrier resin, and an infrared shielding additive package comprising an inorganic infrared shielding additive and carbon black, wherein the weight ratio of inorganic infrared shielding additive to carbon black is about 0.001:1 to about 70:1, and wherein the infrared shielding additive package is present at about 0.001 to about 20 wt % of the combined weights of the carrier resin and infrared shielding additive package.

In another embodiment, a method comprises blending a masterbatch comprising a carrier resin, and an infrared shielding additive package comprising an inorganic infrared shielding additive and carbon black, with a base resin to form a composition; and molding the composition to form protective eyewear, wherein the weight ratio of inorganic infrared shielding additive to carbon black in the infrared shielding additive package is about 0.001:1 to about 70:1; and wherein the masterbatch has infrared shielding additive package present in an amount of about 0.001 to about 20 wt % of the combined weights of the carrier resin and the infrared shielding additive package; and wherein the protective eyewear meet each of the requirements for at least one scale of European Norm EN 169 and/or EN 171.

In another embodiment, a method for producing different types of protective eyewear comprises selecting a masterbatch comprising an infrared shielding additive package comprising at least two additives in a carrier resin; blending the masterbatch with a base resin to form composition; and molding the composition into an article for use in preparing protective eyewear, wherein the protective eyewear so produced meet each of the requirements for at least one scale of European Norm EN 169 and/or EN 171, and wherein the highest and lowest MVR for each composition used to produce a different welding goggle differs by less than or equal to 4 cc/10 minutes at 1.2 Kg at 300° C., wherein the MVR is determined according to ISO 1133.

In yet another embodiment, an article comprises the above-described composition.

DETAILED DESCRIPTION OF THE INVENTION

There is provided a composition comprising a polycarbonate, and an IR shielding additive package comprising a combination of inorganic infrared shielding additive (i.e., a metal boride) with carbon black. Surprisingly, the combination of the inorganic infrared shielding additive and carbon black provides a stronger absorbance in the infrared than that obtained with either the inorganic infrared shielding additive or carbon black individually. This allows for use of a lower combined amount of the inorganic infrared shielding additive and carbon black than would be needed where an inorganic infrared shielding additive is used in the absence of carbon black, to achieve an equivalent infrared absorbance meeting at least one scale of European Norm EN 169 and/or EN 171. This is advantageous because relatively higher levels of either additive can negatively affect the physical performance properties of the polycarbonate.

As stated above, the thermoplastic composition comprises a polycarbonate. As used herein, the terms "polycarbonate", "polycarbonate composition", and "composition comprising aromatic carbonate chain units" includes compositions having structural units of the formula (1):

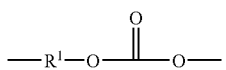

(1)

wherein greater than or equal to about 60 percent of the total number of $R^1$ groups are aromatic organic radicals and the balance thereof are aliphatic, alicyclic, or aromatic radicals. Specifically, $R^1$ is an aromatic organic radical and, more specifically, a radical of the formula (2):

$$-A^1-Y^1-A^2- \quad (2)$$

wherein each of $A^1$ and $A^2$ is a monocyclic divalent aryl radical and $Y^1$ is a bridging radical having zero, one, or two atoms which separate $A^1$ from $A^2$. In an exemplary embodiment, one atom separates $A^1$ from $A^2$. Illustrative examples of the $Y^1$ radicals are —O—, —S—, —S(O)—, —S(O)$_2$—, —C(O)—, methylene, cyclohexyl-methylene, 2-[2,2,1]-bicycloheptylidene, ethylidene, isopropylidene, neopentylidene, cyclohexylidene, cyclopentadecylidene, cyclododecylidene, adamantylidene, or the like. In another embodiment, zero atoms separate $A^1$ from $A^2$, with an illustrative example being biphenyl. The bridging radical $Y^1$ can be a saturated hydrocarbon group such as methylene, cyclohexylidene or isopropylidene.

Polycarbonates may be produced by the Schotten-Bauman interfacial reaction of the carbonate precursor with dihydroxy compounds. Typically, an aqueous base such as sodium hydroxide, potassium hydroxide, calcium hydroxide, or the like, is mixed with an organic, water immiscible solvent such as benzene, toluene, carbon disulfide, or dichloromethane, which contains the dihydroxy compound. A phase transfer agent is generally used to facilitate the reaction. Molecular weight regulators may be added either singly or in admixture to the reactant mixture. Branching agents, described forthwith may also be added singly or in admixture.

Polycarbonates can be produced by the interfacial reaction of dihydroxy compounds in which only one atom separates $A^1$ and $A^2$. As used herein, the term "dihydroxy compound" includes, for example, bisphenol compounds having general formula (3):

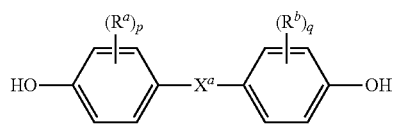

(3)

wherein $R^a$ and $R^b$ each independently represent hydrogen, a halogen atom, specifically bromine, or a monovalent hydrocarbon group, p and q are each independently integers from 0 to 4, and $X^a$ represents one of the groups of formula (4):

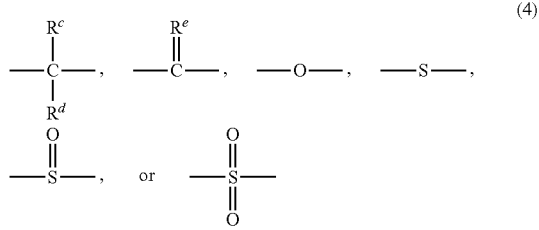

(4)

wherein $R^c$ and $R^d$ each independently represent a hydrogen atom or a monovalent linear or cyclic hydrocarbon group, and $R^e$ is a divalent hydrocarbon group, oxygen, or sulfur.

Examples of the types of bisphenol compounds that may be represented by formula (3) include the bis(hydroxyaryl)alkane series such as, 1,1-bis(4-hydroxyphenyl)methane, 1,1-bis(4-hydroxyphenyl)ethane, 2,2-bis(4-hydroxyphenyl)propane (or bisphenol-A), 2,2-bis(4-hydroxyphenyl)butane, 2,2-bis(4-hydroxyphenyl)octane, 1,1-bis(4-hydroxyphenyl) propane, 1,1-bis(4-hydroxyphenyl)n-butane, bis(4-hydroxyphenyl)phenylmethane, 2,2-bis(4-hydroxy-1-methylphenyl)propane, 1,1-bis(4-hydroxy-t-butylphenyl) propane, 2,2-bis(4-hydroxy-3-bromophenyl)propane, or the like; bis(hydroxyaryl)cycloalkane series such as, 1,1-bis(4-hydroxyphenyl)cyclopentane, 1,1-bis(4-hydroxyphenyl)cyclohexane, or the like, 3,3-bis(4-hydroxyphenyl) phthalimidine, 2-phenyl-3,3-bis-(4-hydroxyphenyl) phthalimidine (PPPBP), or combinations comprising at least one of the foregoing bisphenol compounds.

Other bisphenol compounds that may be represented by formula (3) include those where X is —O—, —S—, —SO— or —S(O)$_2$—. Some examples of such bisphenol compounds are bis(hydroxyaryl)ethers such as 4,4'-dihydroxy diphenylether, 4,4'-dihydroxy-3,3'-dimethylphenyl ether, or the like; bis(hydroxy diaryl)sulfides, such as 4,4'-dihydroxy diphenyl sulfide, 4,4'-dihydroxy-3,3'-dimethyl diphenyl sulfide, or the like; bis(hydroxy diaryl) sulfoxides, such as, 4,4'-dihydroxy diphenyl sulfoxides, 4,4'-dihydroxy-3,3'-dimethyl diphenyl sulfoxides, or the like; bis(hydroxy diaryl)sulfones, such as 4,4'-dihydroxy diphenyl sulfone, 4,4'-dihydroxy-3,3'-dimethyl diphenyl sulfone, or the like; or combinations comprising at least one of the foregoing bisphenol compounds.

Other bisphenol compounds that may be used in the polycondensation of polycarbonate include those of formula (5):

(5)

wherein, $R^f$, is a halogen atom of a hydrocarbon group having 1 to 10 carbon atoms or a halogen substituted hydrocarbon group; n is a value from 0 to 4. When n is at least 2, $R^f$ may be the same or different. Examples of bisphenol compounds that may be represented by the formula (5), are resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, or the like; catechol, hydroquinone, substituted hydroquinones, such as 3-methyl hydroquinone, 3-ethyl hydroquinone, 3-propyl hydroquinone, 3-butyl hydroquinone, 3-t-butyl hydroquinone, 3-phenyl hydroquinone, 3-cumyl hydroquinone, or the like; or combinations comprising at least one of the foregoing bisphenol compounds.

Bisphenol compounds such as 2,2,2',2'-tetrahydro-3,3,3', 3'-tetramethyl-1,1'-spirobi-[1H-indene]-6,6'-diol represented by formula (6) may also be used.

(6)

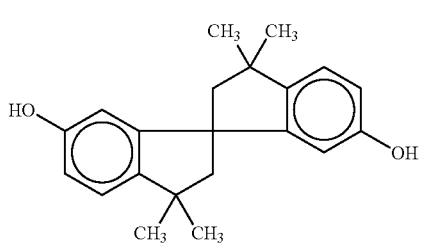

Suitable polycarbonates further include those derived from bisphenols containing alkyl cyclohexane units. Such polycarbonates have structural units corresponding to the formula (7):

(7)

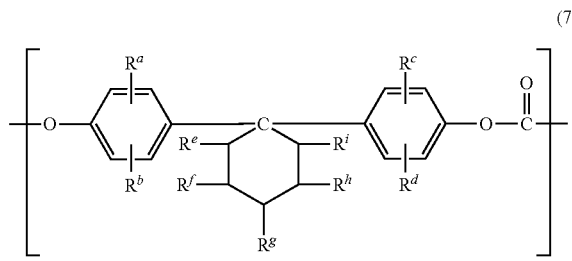

wherein $R^a$-$R^d$ are each independently hydrogen, $C_{1-12}$ alkyl, or halogen; and $R_e$-$R_i$ are each independently hydrogen, $C_{1-12}$ alkyl. The residue may be aliphatic or aromatic, straight-chain, cyclic, bicyclic, branched, saturated, or unsaturated. The alkyl residue may contain heteroatoms over and above the carbon and hydrogen members of the substituent residue. Thus, when specifically noted as containing such heteroatoms, the alkyl residue may also contain carbonyl groups, amino groups, hydroxyl groups, or the like, or it may contain heteroatoms within the backbone of the alkyl residue. Alkyl cyclohexane containing bisphenols, for example the reaction product of two moles of a phenol with one mole of a hydrogenated isophorone, are useful for making polycarbonate polymers with high glass transition temperatures and high heat distortion temperatures. Such isophorone bisphenol-containing polycarbonates have structural units corresponding to the formula (8):

(8)

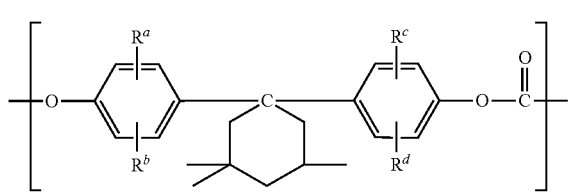

wherein $R_a$-$R_d$ are as defined above. These isophorone bisphenol based polymers, including polycarbonate copolymers made containing non-alkyl cyclohexane bisphenols and blends of alkyl cyclohexyl bisphenol containing polycarbonates with non-alkyl cyclohexyl bisphenol polycarbonates, are supplied by Bayer Co. under the APEC™ trade name. A specifically useful bisphenol compound is bisphenol A.

In one embodiment, the dihydroxy compound may be reacted with a hydroxyaryl-terminated poly(diorganosiloxane) to create a polycarbonate-polysiloxane copolymer. Specifically the polycarbonate-poly(diorganosiloxane) copolymers are made by introducing phosgene under interfacial reaction conditions into a mixture of a dihydroxy compound, such as BPA, and a hydroxyaryl-terminated poly(diorganosiloxane). The polymerization of the reactants can be facilitated by use of a tertiary amine catalyst or a phase transfer catalyst.

The hydroxyaryl-terminated poly(diorganosiloxane) can be made by effecting a platinum catalyzed addition between a siloxane hydride of the formula (9):

(9)

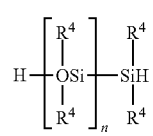

and an aliphatically unsaturated monohydric phenol wherein $R_4$ is, for example, $C_{1-8}$ alkyl radicals, haloalkyl radicals such as trifluoropropyl and cyanoalkyl radicals; aryl radicals such as phenyl, chlorophenyl and tolyl. $R_4$ is specifically methyl, or a mixture of methyl and trifluoropropyl, or a mixture of methyl and phenyl.

Some of the aliphatically unsaturated monohydric phenols, which can be used to make the hydroxyaryl-terminated poly (diorganosiloxane)s are, for example, eugenol, 2-alkylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl-4-propylphenol, 2-allyl-4,6-dimethylphenol, 2-allyl-4-bromo-6-methylphenol, 2-allyl-6-methoxy-4-methylphenol, 2-allyl-4,6-dimethylphenol, or the like, or a combination comprising at least one of the foregoing.

Typical carbonate precursors include the carbonyl halides, for example carbonyl chloride (phosgene), and carbonyl bromide; the bis-haloformates, for example the bis-haloformates of dihydric phenols such as bisphenol A, hydroquinone, or the like, and the bis-haloformates of glycols such as ethylene glycol and neopentyl glycol; and the diaryl carbonates, such as diphenyl carbonate, di(tolyl) carbonate, and di(naphthyl) carbonate. A specific carbonate precursor for the interfacial reaction is carbonyl chloride.

It is also possible to employ polycarbonates resulting from the polymerization of two or more different dihydric phenols or a copolymer of a dihydric phenol with a glycol or with a hydroxy- or acid-terminated polyester or with a dibasic acid or with a hydroxy acid or with an aliphatic diacid in the event a carbonate copolymer rather than a homopolymer is desired for use. Generally, useful aliphatic diacids have about 2 to about 40 carbons. A specifically useful aliphatic diacid is dodecanedioic acid.

Branched polycarbonates, as well as blends of linear polycarbonate and a branched polycarbonate may also be used in the thermoplastic composition. The branched polycarbonates may be prepared by adding a branching agent during polymerization. These branching agents may comprise polyfunctional organic compounds containing at least three functional groups, which may be hydroxyl, carboxyl, carboxylic anhydride, haloformyl, and combinations comprising at least one of the foregoing branching agents. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) α,α-dimethyl benzyl)phenol), 4-chloroformyl phthalic anhydride, trimesic acid, benzophenone tetracarboxylic acid, or the like, or combinations comprising at least one of the foregoing branching agents. The branching agents may be added at a level of about 0.05 to about 4.0 weight percent (wt %), based upon the total weight of the polycarbonate in a given layer.

In one embodiment, the polycarbonate may be produced by a melt polycondensation reaction between a dihydroxy compound and a carbonic acid diester. Examples of the carbonic acid diesters that may be utilized to produce the polycarbonates are diphenyl carbonate, bis(2,4-dichlorophenyl)carbonate, bis(2,4,6-trichlorophenyl) carbonate, bis(2-cyanophenyl) carbonate, bis(o-nitrophenyl) carbonate, ditolyl carbonate, m-cresyl carbonate, dinaphthyl carbonate, bis (diphenyl) carbonate, diethyl carbonate, dimethyl carbonate, dibutyl carbonate, dicyclohexyl carbonate, bis(o-methoxycarbonylphenyl)carbonate, bis(o-ethoxycarbonylphenyl)carbonate, bis(o-propoxycarbonylphenyl)carbonate, bis-ortho methoxy phenyl carbonate, bis(o-butoxycarbonylphenyl)carbonate, bis(isobutoxycarbonylphenyl)carbonate, o-methoxy-carbonylphenyl-o-ethoxycarbonylphenylcarbonate, bis o-(tert-butoxycarbonylphenyl)carbonate, o-ethylphenyl-o-methoxycarbonylphenyl carbonate, p-(tertbutylphenyl)-o-(tert-butoxycarbonylphenyl)carbonate, bis-methyl salicyl carbonate, bis-ethyl salicyl carbonate, bis-propyl salicyl carbonate, bis-butyl salicyl carbonate, bis-benzyl salicyl carbonate, bis-methyl 4-chlorosalicyl carbonate or the like, or combinations comprising at least one of the foregoing carbonic acid diesters. A specifically useful carbonic acid diester is diphenyl carbonate or bis-methyl salicyl carbonate.

The weight average molecular weight of the polycarbonate is about 3,000 to about 1,000,000 grams/mole (g/mole). In one embodiment, the polycarbonate has a molecular weight of about 10,000 to about 100,000 g/mole. In another embodiment, the polycarbonate has a molecular weight of about 20,000 to about 50,000 g/mole. In yet another embodiment, the polycarbonate has a molecular weight of about 25,000 to about 35,000 g/mole.

Cycloaliphatic polyesters may be used in the thermoplastic composition, wherein such polyesters may have optical transparency, improved weatherability, chemical resistance, and low water absorption. It is generally desirable that, where used, cycloaliphatic polyesters have good melt compatibility with the polycarbonates used in the thermoplastic composition. In an exemplary embodiment, a cycloaliphatic polyester that displays good melt compatibility with the polycarbonate can be used in the thermoplastic composition. Cycloaliphatic polyesters are generally prepared by reaction of a diol with a dibasic acid or derivative. The diols useful in the preparation of the cycloaliphatic polyester polymers for use as the high quality optical sheets are straight chain, branched, or cycloaliphatic, and may contain from 2 to 12 carbon atoms.

Examples of suitable diols include ethylene glycol, propylene glycols such as 1,2- and 1,3-propylene glycol, butane diols such as 1,3- and 1,4-butane diol, diethylene glycol, 2,2-dimethyl-1,3-propane diol, 2-ethyl, 2-methyl, 1,3-propane diol, 1,3- and 1,5-pentane diol, dipropylene glycol, 2-methyl-1,5-pentane diol, 1,6-hexane diol, 1,4-cyclohexane dimethanol and particularly its cis- and trans-isomers, triethylene glycol, 1,10-decane diol, and combinations comprising at least one of the foregoing diols. Specifically useful is dimethanol bicyclo octane, dimethanol decalin, a cycloaliphatic diol or chemical equivalents thereof, and particularly 1,4-cyclohexane dimethanol or its chemical equivalents. If 1,4-cyclohexane dimethanol is to be used as the diol component, a mixture of cis- to trans-isomers in ratios of about 1:4 to about 4:1 can be used. Specifically, a ratio of cis- to trans-isomers of about 1:3 can be useful.

The diacids useful in the preparation of the cycloaliphatic polyester polymers are aliphatic diacids that include carboxylic acids having two carboxyl groups each of which are attached to a saturated carbon in a saturated ring. Suitable examples of cycloaliphatic acids include decahydro naphthalene dicarboxylic acid, norbornene dicarboxylic acids, bicyclo octane dicarboxylic acids. Specifically useful cycloaliphatic diacids include 1,4-cyclohexanedicarboxylic acid and trans-1,4-cyclohexanedicarboxylic acids. Linear aliphatic diacids are also useful provided the polyester has at least one monomer containing a cycloaliphatic ring. Illustrative examples of linear aliphatic diacids are succinic acid, adipic acid, dimethyl succinic acid, and azelaic acid. Mixtures of diacid and diols may also be used to make the cycloaliphatic polyesters.

Cyclohexanedicarboxylic acids and their chemical equivalents can be prepared, for example, by the hydrogenation of cycloaromatic diacids and corresponding derivatives such as isophthalic acid, terephthalic acid or naphthalenic acid in a suitable solvent (e.g., water or acetic acid) at room temperature and at atmospheric pressure using catalysts such as rhodium supported on a carrier comprising carbon and alumina. They may also be prepared by the use of an inert liquid medium wherein an acid is at least partially soluble under reaction conditions and a catalyst of palladium or ruthenium in carbon or silica is used.

Generally, during hydrogenation, two or more isomers are obtained in which the carboxylic acid groups are in cis- or trans-positions. The cis- and trans-isomers can be separated by crystallization with or without a solvent, for example, n-heptane, or by distillation. The cis-isomer tends to be more miscible, however, the trans-isomer has higher melting and crystallization temperatures and is specifically suitable. Mixtures of the cis- and trans-isomers may also be used. The weight ratio of trans- to cis-isomer can be about 75:25. When a mixture of isomers or more than one diacid is used, a copolyester or a mixture of two polyesters may be used as the cycloaliphatic polyester polymer.

Chemical equivalents of these diacids including esters may also be used in the preparation of the cycloaliphatic polyesters. Suitable examples of the chemical equivalents of the diacids are alkyl esters, e.g., dialkyl esters, diaryl esters, anhydrides, acid chlorides, acid bromides, and the like, as well as combinations comprising at least one of the foregoing chemical equivalents. Useful chemical equivalents comprise the dialkyl esters of the cycloaliphatic diacids, while a specifically useful chemical equivalent comprises the dimethyl ester of the acid, particularly dimethyl-trans-1,4-cyclohexanedicarboxylate.

Dimethyl-1,4-cyclohexanedicarboxylate can be obtained by ring hydrogenation of dimethylterephthalate, and two isomers having the carboxylic acid groups in the cis- and trans-positions are obtained. Where the isomers can be separated, the trans-isomer is specifically useful. Mixtures of the isomers may also be used as detailed above.

The polyester polymers are generally obtained through the condensation or ester interchange polymerization of the diol or diol chemical equivalent component with the diacid or diacid chemical equivalent component and having recurring units of the formula (10):

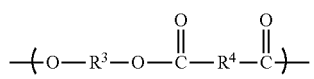
(10)

wherein $R^3$ represents an alkyl or cycloalkyl radical containing 2 to 12 carbon atoms and which is the residue of a straight chain, branched, or cycloaliphatic alkane diol having 2 to 12 carbon atoms or chemical equivalents thereof; and $R^4$ is an alkyl or a cycloaliphatic radical which is the decarboxylated residue derived from a diacid, with the proviso that at least one of $R^3$ or $R^4$ is a cycloalkyl group.

A useful cycloaliphatic polyester is poly(1,4-cyclohexanedimethanol-1,4-cyclohexanedicarboxylate) (PCCD) having recurring units of formula (11):

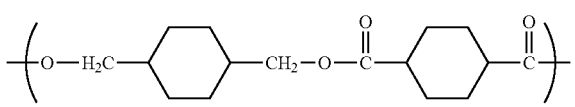
(11)

wherein in the formula (9) $R^3$ is a cyclohexane ring, and wherein $R^4$ is a cyclohexane ring derived from cyclohexanedicarboxylate or a chemical equivalent thereof and is selected from the cis- or trans-isomer or a mixture of cis- and trans-isomers thereof. Cycloaliphatic polyester polymers can be generally made in the presence of a suitable catalyst such as a tetra(2-ethyl hexyl)titanate, in a suitable amount, generally about 50 to 400 ppm of titanium based upon the total weight of the final product.

PCCD is generally completely miscible with the polycarbonate. It is generally desirable for a polycarbonate-PCCD mixture to have a melt volume rate of greater than or equal to about 5 cubic centimeters/10 minutes (cc/10 min or ml/10 min) to less than or equal to about 150 cubic centimeters/10 minutes when measured at 265° C., at a load of 2.16 kilograms and a four minute dwell time. Within this range, it is generally desirable to have a melt volume rate of greater than or equal to about 7, specifically greater than or equal to about 9, and more specifically greater than or equal to about 10 cc/10 min when measured at 265° C., at a load of 2.16 kilograms and a four minute dwell time. Also desirable within this range, is a melt volume rate of less than or equal to about 125, specifically less than or equal to about 110, and more specifically less than or equal to about 100 cc/10 minutes.

Other suitable cycloaliphatic polyesters that may be mixed with the polycarbonate are polyethelene terephthalate (PET), polybutylene terephthalate (PBT), poly(trimethylene terephthalate) (PTT), poly(cyclohexanedimethanol-co-ethylene terephthalate) (PETG), poly(ethylene naphthalate) (PEN), and poly(butylene naphthalate) (PBN).

Another polyester that may be mixed with other polymers are polyarylates. Polyarylates generally refers to polyesters of aromatic dicarboxylic acids and bisphenols. Polyarylate copolymers that include carbonate linkages in addition to the aryl ester linkages, are termed polyester-carbonates, and may also be advantageously utilized in the mixtures. The polyarylates can be prepared in solution or by the melt polymerization of aromatic dicarboxylic acids or their ester forming derivatives with bisphenols or their derivatives.

In general, the polyarylates comprise at least one diphenol residue in combination with at least one aromatic dicarboxylic acid residue. The diphenol residue, illustrated in formula (12), is derived from a 1,3-dihydroxybenzene moiety, referred to throughout this specification as resorcinol or resorcinol moiety. Resorcinol or resorcinol moieties include both unsubstituted 1,3-dihydroxybenzene and substituted 1,3-dihydroxybenzenes.

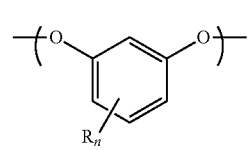
(12)

In formula (10), R is at least one of $C_{1-12}$ alkyl or halogen, and n is 0 to 3. Suitable dicarboxylic acid residues include aromatic dicarboxylic acid residues derived from monocyclic moieties, specifically isophthalic acid, terephthalic acid, or mixtures of isophthalic and terephthalic acids, or from polycyclic moieties such as diphenyl dicarboxylic acid, diphenylether dicarboxylic acid, and naphthalene-2,6-dicarboxylic acid, and the like, as well as combinations comprising at least one of the foregoing polycyclic moieties. A specifically suitable polycyclic moiety is naphthalene-2,6-dicarboxylic acid.

Specifically, the aromatic dicarboxylic acid residues can be derived from mixtures of isophthalic and/or terephthalic acids as generally illustrated in formula (13):

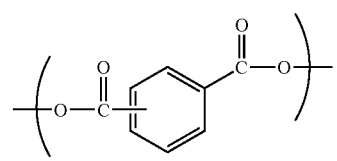
(13)

Therefore, in one embodiment the polyarylates comprise resorcinol arylate polyesters as illustrated in formula (14) wherein R and n are previously defined for formula (11):

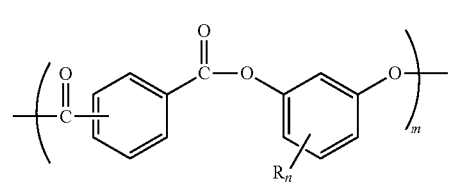
(14)

wherein R is at least one of $C_{1-12}$ alkyl or halogen, n is 0 to about 3, and m is at least about 8. Specifically, R can be hydrogen. Specifically, n is zero and m is about 10 and about 300. The molar ratio of isophthalate to terephthalate is about 0.25:1 to about 4.0:1.

In another embodiment, the polyarylate comprises thermally stable resorcinol arylate polyesters that have polycyclic aromatic radicals as shown in formula (15):

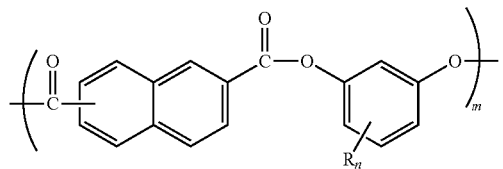

(15)

wherein R is at least one of $C_{1-12}$ alkyl or halogen, n is 0 to about 3, and m is at least about 8.

In another embodiment, the polyarylates are copolymerized to form block copolyestercarbonates, which comprise carbonate and arylate blocks. They include polymers comprising structural units of the formula (16):

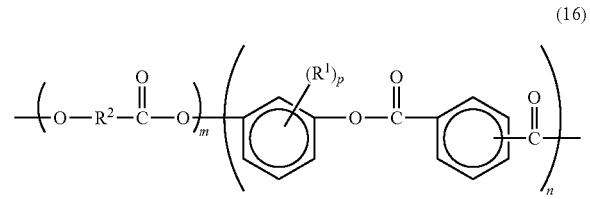

(16)

wherein each $R^1$ is independently halogen or $C_{1-12}$ alkyl, m is at least 1, p is about 0 to about 3, each $R^2$ is independently a divalent organic radical, and n is at least about 4. Specifically n is at least about 10, more specifically at least about 20 and most specifically about 30 to about 150. Specifically m is at least about 3, more specifically at least about 10 and most specifically about 20 to about 200. In an exemplary embodiment m is present in an amount of about 20 and 50.

It is generally desirable for the weight average molecular weight of the polyester to be about 500 to about 1,000,000 grams/mole (g/mole). In one embodiment, the polyester has a weight average molecular weight of about 10,000 to about 200,000 g/mole. In another embodiment, the polyester has a weight average molecular weight of about 30,000 to about 150,000 g/mole. In yet another embodiment, the polyester has a weight average molecular weight of about 50,000 to about 120,000 g/mole. An exemplary molecular weight for the polyester can be 60,000 and 120,000 g/mole. These molecular weights are determined against a polystyrene standard.

The polycarbonate is generally used in amounts of about 70 to about 99.9 weight percent (wt %) based upon the weight of the thermoplastic composition. In one embodiment, the polycarbonate is present in an amount of about 75 to about 99.7 wt %, based on the total weight of the thermoplastic composition. In another embodiment, the polycarbonate is present in an amount of about 80 to about 99.5 wt %, based on the total weight of the thermoplastic composition. In yet another embodiment, the polycarbonate is present in an amount of about 85 to about 97 wt %, based on the total weight of the thermoplastic composition.

The thermoplastic composition further comprises an inorganic infrared (IR) shielding additive, also referred to as an inorganic infrared (IR) absorbing additive. The inorganic infrared shielding additive is substantially evenly dispersed in the thermoplastic composition. As used herein, the term "substantially evenly dispersed" means that the concentration varies by less than 5%, specifically less than 3%, more specifically less than 1%, still more specifically less than 0.5%, and still more specifically less than 0.1%, throughout the thermoplastic composition. Inorganic infrared shielding additives can generally be fine particles of a metal boride and/or a metal oxide. Specific examples of suitable metal borides include, but are not limited to, lanthanum boride ($LaB_6$), praseodymium boride ($PrB_6$), neodymium boride ($NdB_6$), cerium boride ($CeB_6$), gadolinium boride ($GdB_6$), terbium boride ($TbB_6$), dysprosium boride ($DyB_6$), holmium boride ($HoB_6$), yttrium boride ($YB_6$), samarium boride ($SmB_6$), europium boride ($EuB_6$), erbium boride ($ErB_6$), thulium boride ($TmB_6$), ytterbium boride ($YbB_6$), lutetium boride ($LuB_6$), strontium boride ($SrB_6$), calcium boride ($CaB_6$), titanium boride ($TiB_2$), zirconium boride ($ZrB_2$), hafnium boride ($HfB_2$), vanadium boride ($VB_2$), tantalum boride ($TaB_2$), chromium borides ($CrB$ and $CrB_2$), molybdenum borides ($MoB_2$, $Mo_2B_5$ and $MoB$), tungsten boride ($W_2B_5$), or the like, or combinations comprising at least one of the foregoing borides. Specific examples of suitable metal oxides include, but are not limited to, potassium tungsten oxide ($K(WO_3)_3$), rubidium tungsten oxide ($Rb(WO_3)_3$), cesium tungsten oxide ($Cs(WO_3)_3$), thallium tungsten oxide ($Tl(WO_3)_3$), a combination comprising at least one of the foregoing oxides, and the like. An exemplary metal oxide is cesium tungsten oxide ($Cs(WO_3)_3$). A combination comprising at least one of the foregoing borides and at least one of the foregoing oxides may also be used.

The inorganic infrared shielding additives can be in the form of nanosized particles prior to the dispersion in the polycarbonate resin. There is no particular limitation to the shape of the particles, which may be for example, spherical, irregular, plate-like or whisker like. The nanosized particles can have an average largest dimension of less than or equal to about 200 nanometers (nm), specifically less than or equal to about 150 nm, more specifically less than or equal to about 100 nm, still more specifically less than or equal to about 75 nm, and still more specifically less than or equal to about 50 nm. In one embodiment, greater than about 90% of the particles, specifically greater than about 95% of the particles, and more specifically greater than about 99% of the particles have an average largest dimension of less than or equal to about 200 nm. Bimodal or higher particle size distributions may be used. The particles should be sufficiently small such that they do not interfere with the passage of visible light through the polycarbonate resin, at least to the degree that would unacceptably interfere with their use in transparent applications as mentioned above.

The inorganic infrared shielding additive can be used in an amount of about 0.75 to about 10,000 ppm, specifically about 1 ppm to about 5,000 ppm, more specifically about 1.25 ppm to about 1,000 ppm, and still more specifically about 1.5 to about 500 ppm, based on the total amount of the composition.

The inorganic infrared shielding additives are used in the composition in an amount of about 0.01 gram per square meter ($g/m^2$) to about 1.0 $g/m^2$, specifically about 0.0125 to about 0.75 $g/m^2$, more specifically about 0.015 to about 0.6 $g/m^2$, and still more specifically about 0.018 to about 0.56 $g/m^2$, based on the amount of the composition. It will be understood that, where the composition has a concentration of inorganic infrared shielding additive expressed in units of gram/square meter, the amount of inorganic infrared shielding additive in the composition will depend upon the thickness of an article prepared from the composition.

The thermoplastic composition also comprises carbon black, wherein the carbon black is substantially evenly dispersed in the thermoplastic composition. Suitable carbon blacks are those having average particle sizes less than or equal to about 100 nanometers (nm), specifically less than or equal to about 75 nm, more specifically less than or equal to about 50 nm, and even more specifically less than or equal to about 40 nm. In addition, carbon blacks may also have surface area greater than about 20 square meters per gram (m$^2$/g), specifically greater than or equal to about 40 m$^2$/g. The carbon black may have a surface area less than or equal to 175 m$^2$/g, specifically less than or equal to 165 m$^2$/g, and more specifically less than or equal to 155 m$^2$/g. Suitable carbon black is distinguished from conductive carbon black in having minimal or no electrical conductivity. Commercially available carbon blacks are sold under a variety of trade names, and in a number of different forms including dry processed pellets under the trade name BLACK PEARLS™, as wet processed pellets under the trade names ELFTEX™, REGAL™, and CSX™, and in a fluffy form including MONARCH™, ELFTEX™, REGAL™, and MOGUL™, all from Cabot Corporation. These carbon blacks are available in particle sizes of 20 to 50 nanometers (nm) and with surface areas of 35 to 138 square meters per gram (m$^2$/g). A non-limiting example of a specific suitable carbon black is MONARCH™ 800, from Cabot Corporation. In one embodiment, conductive carbon black may be used in addition to (or instead of) the carbon black. The carbon black(s) maybe treated or untreated.

The carbon black can be used in an amount of about 1 to about 27,000 ppm, specifically about 1.5 ppm to about 13,000 ppm, more specifically about 2 ppm to about 3,000 ppm, and still more specifically about 3 to about 1,500 ppm, based on the total weight of the composition.

The carbon black is used in amounts of about 0.001 gram per square meter (g/m$^2$) to about 2.0 g/m$^2$, specifically about 0.005 to about 1.75 g/m$^2$, more specifically about 0.01 to about 1.55 g/m$^2$, and still more specifically about 0.011 to about 1.54 g/m$^2$, based on the total amount of the composition. It will be understood that, where the composition has a concentration of carbon black expressed in units of gram/square meter, the amount of carbon black in the composition will depend upon the thickness of an article prepared from the composition. Again, the carbon black particles should be sufficiently small and present in sufficiently low concentration such that they do not interfere with the passage of visible light through the polycarbonate resin, at least to the degree that would unacceptably interfere with their use in transparent applications as mentioned above.

The inorganic infrared shielding additive can be combined with carbon black to give an infrared shielding additive package, having a weight ratio of inorganic infrared shielding additive to carbon black of about 0.001:1 to about 70:1, specifically about 0.005:1 to about 65:1, more specifically about 0.01:1 to about 60:1. The infrared shielding additive package is present in an amount of about 1 to about 37,000 ppm, specifically about 2.0 to about 35,000 ppm, more specifically about 2.5 to about 33,000 ppm, and still more specifically about 3 to about 32,500 ppm, based on the total weight of the thermoplastic composition.

It has been found that inorganic infrared shielding additives (i.e., metal borides and/or metal oxides described hereinabove) possess both thermal stability and suitable infrared absorbance, are stable to thermal processing conditions of greater than about 260° C., and are dispersible in thermoplastic compositions including polycarbonate resins and blends comprising polycarbonate resins. Addition of such inorganic infrared shielding additives can desirably increase infrared absorbance of polycarbonate resins. However, it has also been observed that adding particulate inorganic infrared shielding additive alone to a polycarbonate resin, can increase the dissipation of incident light, and hence increase the level of haze in the combined polycarbonate resin and inorganic infrared shielding additive. The increase in haze increases approximately linearly with increasing loading of the inorganic infrared shielding additive, and hence the problem of high haze is greater for compositions having higher inorganic infrared shielding additive. Increased haze, i.e., a haze greater than about 5%, can in turn limit the use of the articles. Where an article is used to prepare protective eyewear for use in visually demanding, high infrared emission precision work, it is desirable for safety and accuracy's sake to have high clarity in the article to allow the user thereof view and visually resolve detail.

Haze can be reduced in the composition when an infrared shielding additive package is used which comprises a combination of inorganic IR additive (metal boride) with carbon black. Surprisingly, the combination of inorganic infrared shielding additive and carbon black provides a stronger absorbance in the infrared than that obtained with either the inorganic infrared shielding additive or carbon black individually. This allows for use of a lower combined amount of the inorganic infrared shielding additive and carbon black relative than would be needed for the inorganic infrared shielding additive alone, to achieve an equivalent infrared absorbance. It was found that the composition using a combination of metal boride with carbon black, and therefore having a lower loading of metal boride, also had lower haze values than compositions with equivalent infrared absorbance having metal boride alone, without carbon black. Carbon black thus allows for a reduction in the amount of metal boride needed, thereby keeping the haze low. This is desirable for compositions for use in applications where a highly infrared shielding performance in combination with low haze in the article is desired.

Thus, the composition prepared using an inorganic IR shielding package has a haze of less than or equal to about 5%, specifically less than or equal to about 4%, more specifically less than or equal to about 3%, and still more specifically less than or equal to about 2.8%, as measured at 2.5 millimeters (mm) thickness according to ASTM D1003-00.

It has also been observed that use of concentrations of inorganic infrared shielding additive (i.e., metal borides) at levels of about 1.56 g/m$^2$ or higher can lead to an undesirable increase in MVR for the composition, to give an undesirable MVR for the composition of about 10 cc/10 min. or higher. Increasing levels of inorganic infrared shielding additive increases approximately linearly with increasing MVR. This increased MVR is in turn not desirable for manufacturing during subsequent extrusion. Use of carbon black to decrease the amount of inorganic shielding additive while maintaining performance with respect to the EN 169 and/or EN 171 norms can unexpectedly provide less of an increase in the MVR of the composition. The level of inorganic infrared shielding additive used in the composition can thus be lower, to desirably provide a lower MVR for the composition.

Thus, the composition can have a melt flow rate (MVR) of about 1 to about 8 grams per 10 minutes flow (cc/10 min.), specifically about 1.5 to about 7.5 cc/10 min., and more specifically about 2 to about 7 cc/10 min., as determined at 300° C. and 1.2 Kg according to ISO 1133.

The composition can further comprise a UV absorbing additive. The UV absorbing additive facilitates the preservation of the IR absorbing additive by increasing its hydrolytic stability. Suitable UV absorbing additives are benzophenones such as 2,4 dihydroxybenzophenone, 2-hydroxy-4-methoxybenzophenone, 2-hydroxy-4-n-octoxybenzophenone, 4-dodecyloxy-2 hydroxybenzophenone, 2-hydroxy-4-octadecyloxybenzophenone, 2,2' dihydroxy-4 methoxybenzophenone, 2,2' dihydroxy-4,4'dimethoxybenzophenone, 2,2' dihydroxy-4 methoxybenzophenone, 2,2', 4,4' tetra hydroxybenzophenone, 2-hydroxy-4-methoxy-5 sulfobenzophenone, 2-hydroxy-4-methoxy-2'-carboxybenzophenone, 2,2'dihydroxy-4,4'dimethoxy-5 sulfobenzophenone, 2-hydroxy-4-(2-hydroxy-3-methylaryloxy) propoxybenzophenone, 2-hydroxy-4 chlorobenzopheone, or the like; benzotriazoles such as 2-(2-hydroxy-5-tert-octylphenyl)-benzotriazole, 2-hydroxy-4-n-octoxy benzophenone 2-(2-hydroxy-5-methyl phenyl) benzotriazole, 2-(2-hydroxy-3',5'-di-tert-butyl phenyl) benzotriazole, and 2-(2-hydroxy-X-tert, butyl-5'-methyl-phenyl) benzotriazole, or the like; salicylates such as phenyl salicylate, carboxyphenyl salicylate, p-octylphenyl salicylate, strontium salicylate, p-tert butylphenyl salicylate, methyl salicylate, dodecyl salicylate, or the like; and also other ultraviolet absorbents such as resorcinol monobenzoate, 2 ethyl hexyl-2-cyano, 3-phenylcinnamate, 2-ethyl-hexyl-2-cyano-3,3-diphenyl acrylate, ethyl-2-cyano-3,3-diphenyl acrylate, 2-2'-thiobis(4-t-octylphenolate)-1-n-butylamine, or the like, or combinations comprising at least one of the foregoing UV absorbing additives. Preferred commercially available UV absorbers are TINUVIN™ 234, TINUVIN™ 329, TINUVIN™ 350 and TINUVIN™ 360, commercially available from Ciba Specialty Chemicals; CYASORB™ UV absorbers, available from Cyanamide, such as 2-(2H-benzotriazol-2-yl)-4-(1,1,3,3-tetramethylbutyl)-phenol (CYASORB™ 5411); 2-hydroxy-4-n-octyloxy-benzophenone (CYASORB™ 531); 2-[4,6-bis(2,4-dimethylphenyl)-1,3,5-triazin-2-yl]-5-(octyloxy)-phenol (CYASORB™ 1164); 2,2'-(1,4-phenylene)bis(4H-3,1-benzoxazin-4-one) (CYASORB™ UV-3638); 1,3-bis[(2-cyano-3,3-diphenylacryloyl)oxy]-2,2-bis[[(2-cyano-3,3-diphenylacryloyl)oxy]methyl]propane (UVINUL 3030); 2,2'-(1,4-phenylene) bis(4H-3,1-benzoxazin-4-one); 1,3-bis[(2-cyano-3,3-diphenylacryloyl)oxy]-2,2-bis[[(2-cyano-3,3-diphenylacryloyl)oxy]methyl]propane. For articles formed by extrusion, UVINL™ 3030, commercially available from BASF, is specifically useful due to its low volatility.

The UV absorbers can be used in the composition in amounts of about 0.05 to about 5 wt %, based upon the total weight of the composition. In one embodiment, the UV absorber may be used in an amount of about 0.1 to about 0.5 wt %, specifically about 0.2 to about 0.4 wt %, based on the total weight of the composition.

The composition can contain thermal stabilizers to compensate for the increase in temperature brought on by the interaction of the IR light with the inorganic infrared shielding additives. Further, the addition of thermal stabilizers protects the material during processing operations such as melt blending. In general, an article comprising thermoplastic polymer containing the inorganic infrared shielding additives may experience an increase in temperature of up to about 20° C., upon exposure to light. The addition of thermal stabilizers to the composition improves the long term aging characteristics and increases the life cycle of the article.

In another embodiment thermal stabilizers may be optionally added to the composition to prevent degradation of the organic polymer during processing and to improve heat stability of the article. Suitable thermal stabilizers include phosphites, phosphonites, phosphines, hindered amines, hydroxylamines, phenols, acryloyl modified phenols, hydroperoxide decomposers, benzofuranone derivatives, or the like, or combinations comprising at least one of the foregoing thermal stabilizers. Examples include, but are not limited to, phosphites such as tris(nonyl phenyl) phosphite, tris(2,4-di-t-butylphenyl) phosphite, bis(2,4-di-t-butylphenyl) pentaerythritol diphosphite, distearyl pentaerythritol diphosphite or the like; alkylated monophenols or polyphenols; alkylated reaction products of polyphenols with dienes, such as tetrakis[methylene(3,5-di-tert-butyl-4-hydroxyhydrocinnamate)] methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl)propionate or the like; amides of beta-(3,5-di-tert-butyl-4-hydroxyphenyl)-propionic acid or the like, or combinations comprising at least one of the foregoing antioxidants. Suitable thermal stabilizers that are commercially available are IRGAPHOS™ 168, DOVERPHOS™ S-9228, ULTRANOX™ 641, or the like. If desirable, an optional co-stabilizer such as a aliphatic epoxy or a hindered phenol anti-oxidant such as IRGANOX™ 1076, IRGANOX™ 1010, both from Ciba Specialty chemicals may also be added to improve thermal stability of the composition. The preferred thermal stabilizers are phosphites.

The thermal stabilizer can be present in an amount of about 0.001 to about 3 wt %, specifically about 0.002 to about 1 wt %, more specifically about 0.005 to about 0.5 wt %, and still more specifically about 0.01 to about 0.1 wt %, based on the total weight of the composition.

The composition can optionally further comprise fillers. Suitable fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate (as its anhydride, dihydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as asbestos, carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as cellulose, cotton, sisal, jute, starch, cork flour, lignin, ground nut shells, corn, rice grain husks or the like; organic fillers such as polytetrafluoroethylene; reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, tripoli, diatomaceous earth, or the like, or combinations comprising at least one of the foregoing fillers or reinforcing agents.

The fillers and reinforcing agents may be coated with a layer of metallic material to facilitate conductivity, or surface treated with silanes to improve adhesion and dispersion with the polymeric matrix resin. In addition, the reinforcing fillers may be provided in the form of monofilament or multifilament fibers and may be used either alone or in combination with other types of fiber, through, for example, co-weaving or core/sheath, side-by-side, orange-type or matrix and fibril constructions, or by other methods known to one skilled in the art of fiber manufacture. Suitable cowoven structures include, for example, glass fiber-carbon fiber, carbon fiber-aromatic polyimide (aramid) fiber, and aromatic polyimide fiberglass fiber or the like. Fibrous fillers may be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids. Fillers, where used, can be present in amounts of about 0.01 to about 30 wt %, based on the total weight of the composition.

Plasticizers, lubricants, and/or mold release agents additives may also be used. There is considerable overlap among these types of materials, which include, for example, phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl) phosphate of hydroquinone and the bis(diphenyl) phosphate of bisphenol-A; poly-alpha-olefins; epoxidized soybean oil; silicones, including silicone oils; esters, for example, fatty acid esters such as alkyl stearyl esters, e.g., methyl stearate; stearyl stearate, pentaerythritol tetrastearate, and the like; mixtures of methyl stearate and hydrophilic and hydrophobic nonionic surfactants comprising polyethylene glycol polymers, polypropylene glycol polymers, and copolymers thereof, e.g., methyl stearate and polyethylene-polypropylene glycol copolymers in a suitable solvent; waxes such as beeswax, montan wax, paraffin wax or the like. Such materials can be used in amounts of about 0.0001 to about 1.0 wt %, based on the total weight of the composition.

The term "antistatic agent" refers to monomeric, oligomeric, or polymeric materials that can be processed into polymer resins and/or sprayed onto materials or articles to improve conductive properties and overall physical performance. Examples of monomeric antistatic agents include glycerol monostearate, glycerol distearate, glycerol tristearate, ethoxylated amines, primary, secondary and tertiary amines, ethoxylated alcohols, alkyl sulfates, alkylarylsulfates, alkylphosphates, alkylaminesulfates, alkyl sulfonate salts such as sodium stearyl sulfonate, sodium dodecylbenzenesulfonate or the like, quaternary ammonium salts, quaternary ammonium resins, imidazoline derivatives, sorbitan esters, ethanolamides, betaines, or the like, or combinations comprising at least one of the foregoing monomeric antistatic agents.

Exemplary polymeric antistatic agents include certain polyesteramides polyether-polyamide (polyetheramide) block copolymers, polyetheresteramide block copolymers, polyetheresters, or polyurethanes, each containing polyalkylene glycol moieties polyalkylene oxide units such as polyethylene glycol, polypropylene glycol, polytetramethylene glycol, and the like. Such polymeric antistatic agents are commercially available, for example Pelestat™ 6321 (Sanyo) or Pebax™ MH1657 (Atofina), Irgastat™ P18 and P22 (Ciba-Geigy). Other polymeric materials that may be used as antistatic agents are inherently conducting polymers such as polyaniline (commercially available as PANIPOL®EB from Panipol), polypyrrole and polythiophene (commercially available from Bayer), which retain some of their intrinsic conductivity after melt processing at elevated temperatures. In one embodiment, carbon fibers, carbon nanofibers, carbon nanotubes, carbon black, or any combination of the foregoing may be used in a polymeric resin containing chemical antistatic agents to render the composition electrostatically dissipative.

Antistatic agents that are suitable for use herein include onium salts of alkyl sulfonates, particularly alkylated and arylated onium salts of perfluorinated alkyl sulfonates. Exemplary onium salts are phosphonium, ammonium, sulfonium, imidazolinium, pyridinium or tropilium salt. Preferable are alkylated ammonium and phosphonium salts of perfluorinated alkyl sulfonates. Most preferable alkylated phosphonium sulfonates. Specifically useful phosphonium sulfonates include fluorinated phosphonium sulfonates which can comprise a fluorocarbon containing an organic sulfonate anion, and an organic phosphonium cation. Suitable examples of such organic sulfonate anions include, but are not limited to, perfluoro methane sulfonate, perfluoro butane sulfonate, perfluoro hexane sulfonate, perfluoro heptane sulfonate, perfluoro octane sulfonate, combinations comprising one or more of these, and the like. Suitable examples of the aforementioned phosphonium cation include, but are not limited to, aliphatic phosphonium such as tetramethyl phosphonium, tetraethyl phosphonium, tetrabutyl phosphonium, triethylmethyl phosphonium, tributylmethyl phosphonium, tributylethyl phosphonium, trioctylmethyl phosphonium, trimethylbutyl phosphonium trimethyloctyl phosphonium, trimethyllauryl phosphonium, trimethylstearyl phosphonium, triethyloctyl phosphonium and aromatic phosphoniums such as tetraphenyl phosphonium, triphenylmethyl phosphonium, triphenylbenzyl phosphonium, tributylbenzyl phosphonium, combinations comprising one or more of the foregoing, and the like. Suitable examples of the aforementioned ammonium cation include, but are not limited to, aliphatic ammonium such as tetramethyl ammonium, tetraethyl ammonium, tetrabutyl ammonium, triethylmethyl ammonium, tributylmethyl ammonium, tributylethyl ammonium, trioctylmethyl ammonium, trimethylbutyl ammonium trimethyloctyl ammonium, trimethyllauryl ammonium, trimethylstearyl ammonium, triethyloctyl ammonium and aromatic ammoniums such as tetraphenyl ammonium, triphenylmethyl ammonium, triphenylbenzyl ammonium, tributylbenzyl ammonium, combinations comprising one or more of the foregoing, and the like. A combination comprising at least one of the foregoing antistatic agents may also be used.

Antistatic agents can be used in amounts of about 0.0001 to about 5.0 wt %, based on the total weight of the composition.

Colorants such as pigment and/or dye additives may also be present. Suitable pigments include for example, inorganic pigments such as metal oxides and mixed metal oxides such as zinc oxide, titanium dioxides, iron oxides or the like; sulfides such as zinc sulfides, or the like; aluminates; sodium sulfo-silicates sulfates, chromates, or the like; carbon blacks; zinc ferrites; ultramarine blue; Pigment Brown 24; Pigment Red 101; Pigment Yellow 119; organic pigments such as azos, di-azos, quinacridones, perylenes, naphthalene tetracarboxylic acids, flavanthrones, isoindolinones, tetrachloroisoindolinones, anthraquinones, anthanthrones, dioxazines, phthalocyanines, and azo lakes; Pigment Blue 60, Pigment Red 122, Pigment Red 149, Pigment Red 177, Pigment Red 179, Pigment Red 202, Pigment Violet 29, Pigment Blue 15, Pigment Green 7, Pigment Yellow 147 and Pigment Yellow 150, or combinations comprising at least one of the foregoing pigments. Pigments can be used in amounts of about 0.01 to about 10 wt %, based on the total weight of the composition.

Suitable dyes can be organic materials and include, for example, coumarin dyes such as coumarin 460 (blue), coumarin 6 (green), nile red or the like; lanthanide complexes; hydrocarbon and substituted hydrocarbon dyes; polycyclic aromatic hydrocarbon dyes; scintillation dyes such as oxazole or oxadiazole dyes; aryl- or heteroaryl-substituted poly($C_{2-8}$) olefin dyes; carbocyanine dyes; indanthrone dyes; phthalocyanine dyes; oxazine dyes; carbostyryl dyes; napthalenetetracarboxylic acid dyes; porphyrin dyes; bis(styryl)biphenyl dyes; acridine dyes; anthraquinone dyes; cyanine dyes; methine dyes; arylmethane dyes; azo dyes; indigoid dyes, thioindigoid dyes, diazonium dyes; nitro dyes; quinone imine dyes; aminoketone dyes; tetrazolium dyes; thiazole dyes; perylene dyes, perinone dyes; bis-benzoxazolylthiophene (BBOT); triarylmethane dyes; xanthene dyes; thioxanthene dyes; naphthalimide dyes; lactone dyes; fluorophores such as anti-stokes shift dyes which absorb in the near infrared wavelength and emit in the visible wavelength, or the like; luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3'''',5''''-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H-pyran; 1,1'-diethyl-2,2'-carbocyanine iodide; 3,3'-diethyl-4,4',5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene; chrysene; rubrene; coronene, or the like, or combinations comprising at least one of the foregoing dyes. Dyes can be used in amounts of about 0.01 to about 10 wt %, based on the total weight of the composition.

Halogenated materials may be used as flame retardants, for example halogenated compounds and resins of formula (17):

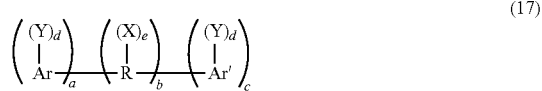

(17)

wherein R is an alkylene, alkylidene or cycloaliphatic linkage, e.g., methylene, ethylene, propylene, isopropylene, isopropylidene, butylene, isobutylene, amylene, cyclohexylene, cyclopentylidene, or the like; or an oxygen ether, carbonyl, amine, or a sulfur containing linkage, e.g., sulfide, sulfoxide, sulfone, or the like. R can also consist of two or more alkylene or alkylidene linkages connected by such groups as aromatic, amino, ether, carbonyl, sulfide, sulfoxide, sulfone, or the like.

Ar and Ar' in formula (17) are each independently mono- or polycarbocyclic aromatic groups such as phenylene, biphenylene, terphenylene, naphthylene, or the like.

Y is an organic, inorganic, or organometallic radical, for example: halogen, e.g., chlorine, bromine, iodine, fluorine; or ether groups of the general formula OE, wherein E is a monovalent hydrocarbon radical similar to X; or monovalent hydrocarbon groups of the type represented by R; or other substituents, e.g., nitro, cyano, and the like, said substituents being essentially inert provided that there is at least one and preferably two halogen atoms per aryl nucleus.

When present, each X is independently a monovalent hydrocarbon group, for example an alkyl group such as methyl, ethyl, propyl, isopropyl, butyl, decyl, or the like; an aryl groups such as phenyl, naphthyl, biphenyl, xylyl, tolyl, or the like; and aralkyl group such as benzyl, ethylphenyl, or the like; a cycloaliphatic group such as cyclopentyl, cyclohexyl, or the like. The monovalent hydrocarbon group may itself contain inert substituents.

Each d is independently 1 to a maximum equivalent to the number of replaceable hydrogens substituted on the aromatic rings comprising Ar or Ar'. Each e is independently 0 to a maximum equivalent to the number of replaceable hydrogens on R. Each a, b, and c is independently a whole number, including 0. When b is not 0, neither a nor c may be 0. Otherwise either a or c, but not both, may be 0. Where b is 0, the aromatic groups are joined by a direct carbon-carbon bond.

The hydroxyl and Y substituents on the aromatic groups, Ar and Ar' can be varied in the ortho, meta or para positions on the aromatic rings and the groups can be in any possible geometric relationship with respect to one another.

Included within the scope of the above formula are bisphenols of which the following are representative: 2,2-bis-(3,5-dichlorophenyl)-propane; bis-(2-chlorophenyl)-methane; bis (2,6-dibromophenyl)-methane; 1,1-bis-(4-iodophenyl)-ethane; 1,2-bis-(2,6-dichlorophenyl)-ethane; 1,1-bis-(2-chloro-4-iodophenyl)ethane; 1,1-bis-(2-chloro-4-methylphenyl)-ethane; 1,1-bis-(3,5-dichlorophenyl)-ethane; 2,2-bis-(3-phenyl-4-bromophenyl)-ethane; 2,6-bis-(4,6-dichloronaphthyl)-propane; 2,2-bis-(2,6-dichlorophenyl)-pentane; 2,2-bis-(3,5-dibromophenyl)-hexane; bis-(4-chlorophenyl)-phenyl-methane; bis-(3,5-dichlorophenyl)-cyclohexylmethane; bis-(3-nitro-4-bromophenyl)-methane; bis-(4-hydroxy-2,6-dichloro-3-methoxyphenyl)-methane; and 2,2-bis-(3,5-dichloro-4-hydroxyphenyl)-propane 2,2 bis-(3-bromo-4-hydroxyphenyl)-propane. Also included within the above structural formula are: 1,3-dichlorobenzene, 1,4-dibromobenzene, 1,3-dichloro-4-hydroxybenzene, and biphenyls such as 2,2'-dichlorobiphenyl, polybrominated 1,4-diphenoxybenzene, 2,4'-dibromobiphenyl, and 2,4'-dichlorobiphenyl as well as decabromo diphenyl oxide, and the like.

Also useful are oligomeric and polymeric halogenated aromatic compounds, such as a copolycarbonate of bisphenol A and tetrabromobisphenol A and a carbonate precursor, e.g., phosgene. Metal synergists, e.g., antimony oxide, may also be used with the flame retardant. When used, halogen containing flame retardants can be present in amounts of about 0.1 to about 10 wt %, based on the total weight of the composition.

Inorganic flame retardants may also be used, for example salts of $C_{2-16}$ alkyl sulfonate salts such as potassium perfluorobutane sulfonate (Rimar salt), potassium perfluoroctane sulfonate, tetraethylammonium perfluorohexane sulfonate, and potassium diphenylsulfone sulfonate, and the like; salts formed by reacting for example an alkali metal or alkaline earth metal (for example lithium, sodium, potassium, magnesium, calcium and barium salts) and an inorganic acid complex salt, for example, an oxo-anion, such as alkali metal and alkaline-earth metal salts of carbonic acid, such as $Na_2CO_3$, $K_2CO_3$, $MgCO_3$, $CaCO_3$, and $BaCO_3$ or fluoroanion complex such as $Li_3AlF_6$, $BaSiF_6$, $KBF_4$, $K_3AlF_6$, $KAlF_4$, $K_2SiF_6$, and/or $Na_3AlF_6$ or the like. When present, inorganic flame retardant salts can be present in amounts of about 0.1 to about 5 wt %, based on the total weight of the composition.

Radiation stabilizers may also be present in the composition, specifically gamma-radiation stabilizers. Suitable gamma-radiation stabilizers include diols, such as ethylene glycol, propylene glycol, 1,3-propanediol, 1,2-butanediol, 1,4-butanediol, meso-2,3-butanediol, 1,2-pentanediol, 2,3-pentanediol, 1,4-pentanediol, 1,4-hexandiol, and the like; alicyclic alcohols such as 1,2-cyclopentanediol, 1,2-cyclohexanediol, and the like; branched acyclic diols such as 2,3-dimethyl-2,3-butanediol (pinacol), and the like, and polyols, as well as alkoxy-substituted cyclic or acyclic alkanes. Alkenols, with sites of unsaturation, are also a useful class of alcohols, examples of which include 4-methyl-4-penten-2-ol, 3-methyl-pentene-3-ol, 2-methyl-4-penten-2-ol, 2,4-dimethyl-4-pene-2-ol, and 9-decen-1-ol. Another class of suitable alcohols is the tertiary alcohols, which have at least one hydroxy substituted tertiary carbon. Examples of these include 2-methyl-2,4-pentanediol (hexylene glycol), 2-phenyl-2-butanol, 3-hydroxy-3-methyl-2-butanone, 2-phenyl-2-butanol, and the like, and cycoloaliphatic tertiary carbons such as 1-hydroxy-1-methyl-cyclohexane. Another class of suitable alcohols is hydroxymethyl aromatics, which have hydroxy substitution on a saturated carbon attached to an unsaturated carbon in an aromatic ring. The hydroxy substituted saturated carbon may be a methylol group ($—CH_2OH$) or it may be a member of a more complex hydrocarbon group such as would be the case with ($—CR^4HOH$) or ($—CR_2^4OH$) wherein $R^4$ is a complex or a simply hydrocarbon. Specific hydroxy methyl aromatics may be benzhydrol, 1,3-benzenedimethanol, benzyl alcohol, 4-benzyloxy benzyl alcohol and benzyl benzyl alcohol. Specific alcohols are 2-methyl-2,4-pentanediol (also known as hexylene glycol), polyethylene glycol, polypropylene glycol. Gamma-radiation stabilizing compounds can be used in amounts of 0.001 to 1 wt %, more specifically 0.01 to 0.5 wt %, based on the total weight of the composition.

In an embodiment, the composition comprises a polycarbonate resin, about 0.01 to about 1.0 g/m² of inorganic infrared shielding additive, and about 0.001 to about 2.0 g/m² of carbon black. In another embodiment, the composition comprises a polycarbonate resin, about 0.0125 to about 0.75 g/m² of inorganic infrared shielding additive, and about 0.005 to about 1.75 g/m² of carbon black. In another embodiment, the composition comprises a polycarbonate resin, about 0.015 to about 0.6 g/m² of inorganic infrared shielding additive, and about 0.01 to about 1.55 g/m² of carbon black. In another embodiment, the composition comprises a polycarbonate resin, about 0.018 to about 0.56 g/m² of inorganic infrared shielding additive, and about 0.011 to about 1.54 g/m² of carbon black. The composition can comprise additional components including UV stabilizers, thermal stabilizers, fillers, flame retardants, plasticizers, antioxidants, light stabilizers, plasticizers, colorants, antistatic agents, gamma ray stabilizers, a combination comprising one or more of the foregoing, and the like, insofar as the use of additional components does not adversely affect the desired properties of the composition. The composition thus comprises polycarbonate resin, inorganic infrared shielding additive, carbon black, and optionally any additional components, where the combined weight percentages of all components used totals 100 wt % of the composition.

The compositions may be manufactured by methods generally available in the art, for example, in one embodiment, in one manner of proceeding, powdered or granulated polycarbonate resin, inorganic infrared shielding additive, carbon black, UV additive, thermal stabilizer, and any optional components are first blended in a HENSCHEL-Mixer® high speed mixer. Other low shear processes including but not limited to hand mixing may also accomplish this blending. The blend is then fed into the feedthroat of a twin-screw extruder via a hopper. Alternatively, one or more of the components may be incorporated into the composition by feeding directly into the extruder at the feedthroat and/or a downstream feedport. Such additives may also be compounded into a masterbatch with a desired polymeric resin and fed into the extruder. The extruder is generally operated at a temperature higher than that necessary to cause the composition to flow. The extrudate is immediately quenched in a water batch and pelletized. The pellets, so prepared, when cutting the extrudate may be one-fourth inch long or less as desired. Such pellets may be used for subsequent molding, shaping, or forming.

A masterbatch can be prepared for use with a base resin to prepare the composition. As used herein, the term "masterbatch" refers to a dispersion of particles in a carrier resin, and typically is in the form of a pellet or bead formed using a mixing process such as a compounding/extrusion process. Also as used herein, the term "masterblend" generally refers to a dispersion of the marked particles in a powder carrier. Preparing the masterbatch comprises melt combining a masterblend comprising a carrier resin, an infrared shielding additive package comprising the inorganic infrared shielding additive and carbon black, and optionally any desired additional components such as, for example, the UV additive and/or thermal stabilizer. In one embodiment, the carrier resin is a polycarbonate resin. The masterbatch can be melt combined with a base resin and other additives to form the composition. In one embodiment, the base resin is a polycarbonate resin. In another embodiment, the base resin is the same as the carrier resin used to prepare the masterbatch. The masterbatch can be combined with the base resin as described above using a mixer, and extruded. In one embodiment, the masterbatch and base resin are combined at the feedthroat of an extruder. In another embodiment, the base resin is added to the feedthroat of the extruder, and the masterbatch is added to a downstream feedport of the extruder.

In an embodiment, the masterbatch comprises a carrier resin and infrared shielding package, where the infrared shielding additive package is present at about 0.0001 to about 20 wt % of the combined weights of the carrier resin and infrared shielding additive package, and the infrared shielding additive package has a weight ratio of inorganic infrared shielding additive to carbon black of about 0.001:1 to about 70:1. In another embodiment, the composition comprises a carrier resin and infrared shielding package, where the infrared shielding additive package is present at about 0.005 to about 15 wt % of the combined weights of the carrier resin and infrared shielding additive package, and the infrared shielding additive package has a weight ratio of inorganic infrared shielding additive to carbon black of about 0.005:1 to about 65:1. In another embodiment, the composition comprises a carrier resin and infrared shielding package, where the infrared shielding additive package is present at about 0.001 to about 10 wt % of the combined weights of the carrier resin and infrared shielding additive package, and the infrared shielding additive package has a weight ratio of inorganic infrared shielding additive to carbon black of about 0.01:1 to about 60:1.

The masterbatch is added to the base resin in an amount of about 1 to about 80 wt %, specifically about 2 to about 60 wt %, more specifically about 3 to about 40 wt %, still more specifically about 5 to about 30 wt %, and still more specifically about 10 to about 20 wt % based on the combined weight of the masterbatch and the base resin.

The composition may be processed into articles such as films, sheets, multiwall sheets, plaques, and the like. The composition is generally compounded and either melt or solution blended in devices that can impart shear to the composition to disperse the inorganic IR absorbing additive and the UV absorbing additive. It is desirable to melt blend the composition. Suitable examples of such blending devices are extruders (e.g., single and twin screw extruders), Buss-kneaders, helicones, Waring® blenders, HENSCHEL-Mixers®, Banbury® mixers, a molding machine such as an injection molding machine, a blow molding machine, a vacuum forming machine, and the like. When the composition is melt blended in an extruder, Buss-kneader, Banbury® mixer, helicone, Waring® Blender, HENSCHEL-Mixers®, or the like, it may be optionally desirable to further subject the melt blend to additional shearing in a roll mill. A preferred method of blending is in an injection molding machine.

In one embodiment, in the extrusion of an article from the composition, the additives (e.g., inorganic IR absorbing additive, carbon black, and the UV absorbing additive) may be added to the extruder along with the polycarbonate resin at the feedthroat. In another embodiment, in the extrusion of the article, the additives may be added to the extruder in the form of a masterbatch. While the polycarbonate resin is fed to the feedthroat of the extruder, the masterbatch may be fed either at the feedthroat of the extruder or at a downstream feedport. In one exemplary embodiment, in the production of the article, the polycarbonate resin is fed to the feedthroat of a single or twin screw extruder while the inorganic IR absorbing additive, carbon black, and the UV absorbing additive are added in masterbatch form to a downstream feedport.

The articles manufactured from the compositions can be layers such as for example films, sheets, plaques, or other molded articles. A film is a layer having a thickness of about 0.1 to about 1000 micrometers, while in general a sheet, plaque, or other molded article has a thickness of greater than about 1000 micrometers to about 20 millimeters (mm).

In a specific embodiment, the article can have a thickness of about 0.05 to about 20 millimeters (mm), specifically about 0.1 to about 15 mm, more specifically about 0.5 to about 12 mm, and still more specifically about 1 to about 10 mm.

In one embodiment, articles manufactured from the composition may comprise single-layered or multilayered films or sheets. Single-layered films or sheets may generally be produced by extrusion (i.e., film or sheet extrusion). Multi-layered films or sheets may generally be produced by extrusion followed by laminating the films or sheets in a roll mill or a roll stack. The extrusion of the individual layers of the single or multilayered film or sheet may be performed in a single screw extruder or in a twin screw extruder. It is desirable to extrude the layers in a single or twin screw extruder and to laminate the layers in a roll mill. It is more desirable to co-extrude the layers in a single screw extruder or twin screw extruder and to optionally laminate the layers in a roll mill. The roll mill may be either a two roll or three roll mill, as is desired. Where desired, the layers can be coextruded using single screw extruders for manufacturing of the multilayered film or sheet.

In a multiwall article, the respective sheets that constitute the multiwall may have similar or different compositions as desired. In one embodiment, related to the manufacturing of multiwall articles such as films or sheets, the desired compositions for the article may be separately precompounded prior to coextrusion. In this event, the precompounded composition(s) may be first melt blended in a twin screw extruder, single screw extruder, Buss kneader, roll mill, or the like, prior to being formed into a suitable shapes such as pellets, sheets, and the like, for further co-extrusion. The precompounded compositions may then be fed into the respective extruders for co-extrusion.

As stated above, where a multilayered structure is desired, the layers of the multilayered articles are co-extruded (i.e., prepared by multilayer coextrusion). In one embodiment, in one manner of co-extruding of the multilayered sheet, the melt streams (extrudates) from the various extruders are fed into a feed block die where the various melt streams are combined before entering the die. In another embodiment, the melt streams from the various extruders are fed into a multi-manifold internal combining die. The different melt streams enter the die separately and join just inside the final die orifice. In yet another embodiment, the melt streams from the various extruders are fed into a multi-manifold external combining die. The external combining dies have completely separate manifolds for the different melt streams as well as distinct orifices through which the streams leave the die separately, joining just beyond the die exit. The layers are combined while still molten and just downstream of the die. An exemplary die used in the production of the multilayered sheet is a feed block die. In an exemplary embodiment, the extruders used for the co-extrusion of the respective layers of the multilayer sheet are single screw extruders respectively. The co-extruded sheet may optionally be calendared in a roll mill if desired. The multilayered sheet can have a thickness of about 0.5 to about 35 millimeters.

In yet another embodiment, the composition may be subjected to molding either prior to or after extrusion to manufacture an infrared (IR) absorbent article. The molding can be by injection molding, compression molding, extrusion molding, blow molding, or a combination comprising one of these. Molding may be followed by further processing such as shaping, thermoforming, cold-forming, cutting, coating, or a combination comprising one or more of these processes.

Equipment for melt-flowing the compositions, such as, for example, injection molders, extruders, and the like, can be adjusted to accommodate the MVR of compositions flowing through them, to optimize the molding process for best properties and appearance. European Norms 169 and 171 each describe a wide range of infrared absorbance performance targets for articles, with specific sets of requirements for infrared, and visible and/or ultraviolet absorbance, defined in each scale listed for each of the norms. For the most efficient manufacture of articles for use in protective eyewear, wherein the article does not vary in shape or size, but can with respect to the scale requirements, it is desirable to limit adjustments to the process to the compositions used in manufacturing the articles, and to minimize the adjustments to the manufacturing equipment. Manufacture of different articles meeting the requirements of different scales within either one or both of the norms, using one or more of the above described processes, can be simplified when the melt-flow rate (MVR) is consistent between compositions prepared individually for articles having different scale requirements. It is therefore desirable that the melt flow properties of a composition be consistent to minimize the adjustments made to the manufacturing equipment. Use of infrared shielding additive packages which comprise inorganic infrared shielding additives and carbon black can provide consistent MVR values for compositions prepared therewith, wherein the compositions can meet a given scale requirements for EN 169 and/or EN 171.

Thus, compositions useful for meeting the requirements for any one of the scale requirements of European Norms EN 169 and/or EN 171, can vary in MVR from another composition meeting the requirements for a different scale requirement of EN 169 and/or EN 171, by an amount of less than or equal to about 4 cubic centimeters per 10 minutes of flow (cc/10 min.), specifically less than or equal to about 3.5 cc/10 min., more specifically less than or equal to about 3 cc/10 min., and still more specifically less than or equal to about 2.5 cc/10 min., as measured at 300° C. and 1.2 Kg, according to ISO 1133.

Desirable scale requirements for EN 169 and/or EN 171 are determined, and can be achieved in an article prepared from the composition by selecting a suitable infrared shielding additive package for use in manufacturing as described above. An infrared shielding additive package so selected, that is present in an amount sufficient to meet at least one of the above EN requirements and additionally provides a desirable haze and MVR, has the lowest loading of the inorganic infrared shielding additive and a loading of carbon black which combined provides the optimum infrared shielding for the loading of inorganic infrared shielding additive used, and which has the desired performance as described above. In an embodiment, masterbatches, each comprising a carrier resin and IR shielding additive package, can be prepared as described above and blended with base resin and any desired additives to form compositions such that multiple different scale requirements can be met using the masterbatches, wherein the masterbatches are selected for the above desired properties (i.e., scale requirements, haze, MVR) they afford to the composition. In another embodiment, two or more masterbatches can be prepared, each of which is useful to meet a different scale requirement for EN 169 and/or EN 171 as described above, and can be selected for and combined in different proportions with a base resin such that multiple different scale requirements can be met using the two or more masterbatches.

The article manufactured from the composition desirably absorbs an amount of infrared (IR) radiation. In one embodiment, IR radiation is radiation in the near infrared (NIR) spectral region having a wavelength of 780 to 2000 nanometers (nm). In another embodiment, IR radiation is radiation in the near infrared (NIR) spectral region having a wavelength of 780 to 1400 nanometers (nm). The article may absorb an amount of greater than or equal to about 5%, specifically greater than or equal to about 20%, more specifically greater than or equal to about 30%, still more specifically greater than or equal to about 40%, still more specifically greater than or equal to about 50%, still more specifically greater than or equal to about 60% and still more specifically greater than or equal to about 99.99% of the IR radiation incident upon the surface of the article.

While it is desirable for the article to absorb as much electromagnetic radiation as possible in the IR region of the electromagnetic spectrum, it can also be desirable for the article to be transparent and or to shield light in the visible region of the electromagnetic spectrum. The visible region of the electromagnetic spectrum generally has wavelengths of about 400 to about 700 nm. Thus, the article can have a percent transmission of light in the visible region of less than or equal to about 20%, specifically less than or equal to about 30%, more specifically less than or equal to about 40%, still more specifically less than or equal to about 50%, and still more specifically less than or equal to about 75% as measured using 2.5 mm thickness according to ASTM D1003-00.

It is generally desirable for the article obtained from the composition to have no loss in IR absorption capabilities over a period of greater than or equal to about 2 years, specifically greater than or equal to about 10 years. In one embodiment, a loss in IR absorption capabilities (measured as loss in effective IR absorber content) may be less than or equal to about 7%, specifically less than or equal to about 5%, and more specifically less than or equal to about 4% over a period of 2 years when exposed to ambient environmental conditions. In another embodiment, the loss in IR absorption capabilities may be less than or equal to about 10% over a period of 10 years when exposed to ambient environmental conditions. The loss in IR absorption is measured as the difference between the initial amount of active IR absorption additive and the final amount of active IR absorption additive divided by the initial amount of IR absorption additive after a desired time period has elapsed.

Articles produced from the composition may be advantageously used in protective eyewear or other personal protective equipment (referred to in the art as "PPE") applications exposure to harmful IR, UV or visible radiation is undesirable. Such applications include welding, glassblowing, foundry, metallurgy, metalsmithing, ceramic firing, other kiln and/or furnace operation, other high temperature work, and the like. Articles prepared from the compositions described above meet at least one of the scale requirements for European Norm EN 169 and/or EN 171.

In one embodiment, a method for producing different types of protective eyewear comprises selecting a masterbatch comprising an infrared shielding additive package comprising at least two additives in a carrier resin, blending the masterbatch with a base resin to form composition; and molding the composition into an article for use in preparing protective eyewear. The protective eyewear so produced meet each of the requirements for at least one scale of European Norm EN 169 and/or EN 171. Further, the highest and lowest MVR for compositions used to produce different protective eyewear, produced according to different scale requirements of EN 169 and/or EN 171, differ by less than or equal to 4, preferably less than or equal to 2, more preferably less than or equal to 1 cc/10 minutes at 300° C. and 1.2 Kg according to ISO 1133.

In one embodiment, for example, the protective eyewear prepared using the articles can be welding goggles. In another embodiment, for example, the protective eyewear can be a visor plate for a welder's mask. In another embodiment, for example, the protective eyewear can be goggles for foundry work and/or glassblowing. One skilled in the art will appreciate that the protective eyewear so prepared from the articles can be used for a variety of different applications, for which eye protection from harmful infrared and/or visible radiation is desirable. Thus, any applications either stated or implied in the foregoing examples should not be considered as limiting the use of the article and/or protective eyewear thereto.

In one embodiment, the article may optionally be coated with a coating to enhance various surface properties. The coating may be applied to improve scratch resistance, fog resistance, or the like, to improve antistatic properties, to facilitate easy cleaning of the surface, to provide anti-reflection properties, and the like.

The compositions are further illustrated by the following non-limiting examples.

The compositions were prepared by compounding on a Werner and Pfleider 25 mm intermeshing twin screw extruder at 300 rpm with barrel temperatures 40-200-250-285-300-

300-300-300° C. The color plaques used for this study were molded on an Engel 75T molding apparatus having 4 temperature zones set at 280-290-300-295° C. (mold temperature 90° C.).

Polymer molecular weight was determined by gel permeation chromatography (GPC) using a crosslinked styrene-divinylbenzene gel column, a sample concentration of about 1 milligram per milliliter, and was calibrated using polycarbonate standards. Melt-volume flow rate (MVR) measurements were done at 300° C. and 1.2 Kg according to ISO 1133. Pre-drying of the polycarbonate granulate was done at 120° C. for 2 hours. Haze and transmission (% T) were measured on 2.5 millimeter color plaques according to ASTM D1003-00. The broadband spectral transmission was measured on a Hitachi U4100 spectrophotometer. The transmission data from the Hitachi U4100 were used to indicate 'pass' or 'fail' for the examples according to European Norms EN 169 and EN 171 for the different scales.

The components used to prepare the materials used in the examples and comparative examples are listed in Table 1, below.

TABLE 1

| Component | Material type | Trade Name | Source |
|---|---|---|---|
| PC | Bisphenol-A Polycarbonate resin (powder), Mw = 30,500 | Lexan ™ | GE Plastics |
| UV5411 | UV absorber | Cyasorb ™ UV5411 Light Absorber | Cytec |
| I-168 | (tris(2,4-di-(tert)-butylphenyl) phosphite) (stabilizer) | Irgafos ™ 168 | Great Lakes Chemical |
| CB | Carbon Black | Monarch ™ 800 Carbon Black | Cabot B.V. |
| $LaB_6$ | Lanthanum Hexaboride | KHCS-06 (CAS # 12008-21-8) | Sumitomo Metal Mining Co. Ltd. |

For the examples and comparative examples below, the base polycarbonate composition was prepared using PC resin containing 0.3 wt % UV5411, and 500 ppm of I-168. The concentration of $LaB_6$ and carbon black is expressed in the data below in grams per square meter of layer sample.

Example 1 and Comparative Examples 1 and 2

The following examples and comparative examples were prepared using loadings of $LaB_6$ (all) and carbon black (Ex. 1) selected to demonstrate the balance of properties between meeting EN 171 requirements and MVR performance. The results for the spectral requirements for the examples and comparative examples are summarized as pass or fail (EN 171).

TABLE 2

| | Example 1[a] | Comp. Ex. 1[a] | Comp. Ex. 2[a] |
|---|---|---|---|
| $LaB_6$ (g/m²) | 0.48 | 1.56 | 0.48 |
| CB (g/m²) | 0.24 | 0 | 0 |
| EN 171 Requirements (scale: 5)[b] | Pass | Pass | Fail |
| MVR at 300 C. and 1.2 Kg (cc/10 min) | 7 | 10 | 7 |

[a]All examples and comparative examples are 1.0 mm in thickness.
[b]EN 171 scale 5 requirements are: Luminous transmittance max. 3.2%, min. 1.2%; Maximum mean spectral transmittance in the infrared (% $T_{NIR}$) for 780-1400 nm is 0.71%, and for 780-2000 nm is 10.6%.

The data in Table 2 show a significant difference in MVR values after replacing part of the $LaB_6$ with carbon black. Both Example 1 and Comparative Example 1 meet the EN 171 scale 5 requirements, but Comparative Example 1 has a significantly higher MVR, which can have an adverse effect on visor material production (e.g., the extrusion molding process). Comparative Example 2 having the same $LaB_6$ loading as Example 1 but without CB, has acceptable MVR but does not meet the EN 171 scale 5 standards.

For comparative purposes, FIG. 1 is included which shows the relationship between MVR and $LaB_6$ loading for polycarbonate compositions having these components. FIG. 1 shows MVR for compositions with increasing loadings of $LaB_6$ from 0 wt % to 0.32 wt % added $LaB_6$. Increasing the loading of $LaB_6$ over this range causes an increase in MVR from an initial MVR of 5.3 cc/10 min at 0 wt % added $LaB_6$ to 21.5 cc/10 min. at an $LaB_6$ loading of 0.32 wt % added $LaB_6$. Thus, these results show a strong dependency of MVR on $LaB_6$ loading.

Examples 2 and 3 and Comparative Examples 3-6

The following examples and comparative examples were prepared using loadings of $LaB_6$ (all) and carbon black (Ex. 2 and 3) to demonstrate the balance of properties between meeting EN 169 requirements and haze performance. The results for the spectral requirements for the examples and comparative examples are summarized as pass or fail (EN 169).

TABLE 3

| | | Ex. 2 | Comp Ex 3 | Comp Ex. 4 | Ex. 3 | Comp Ex. 5 | Comp Ex. 6 |
|---|---|---|---|---|---|---|---|
| $LaB_6$ (g/m²) | | 0.2475 | 0.45 | 0.2475 | 0.09564 | 0.14625 | 0.09564 |
| CB (g/m²) | | 0.03825 | 0 | 0 | 0.010688 | 0 | 0 |
| EN169 | Scale 1.7[d] | — | — | — | pass | pass | fail |
| | Scale 2.5[e] | pass | pass | fail | — | — | — |
| Haze | | 2.2 | 2.8 | 2.1 | 1.4 | 1.8 | 1.3 |

[c]All examples and comparative examples are 2.5 mm in thickness.
[d]EN 169 scale 1.7 requirements are: Maximum UV spectral transmittance: 0.0003% at 313 nm, 22.0% at 365 nm; Luminous transmittance max. 58.1%, min. 43.2%; Maximum mean spectral transmittance in the infrared (% $T_{NIR}$) for 780-1400 nm is 40.0%.
[e]EN 169 scale 2.5 requirements are: Maximum UV spectral transmittance: 0.0003% at 313 nm, 6.4% at 365 nm; Luminous transmittance max. 29.1%, min. 17.8%; Maximum mean spectral transmittance in the infrared (% $T_{NIR}$) for 780-1400 nm is 15.0%.

The data in Table 3 shows the difference in haze when $LaB_6$ is combined with carbon black, as compared to a formulation where $LaB_6$ alone is used. Both Example 2 and Comparative Example 3 meet the scale 2.5 transmission requirements (EN 169), but replacing part of the $LaB_6$ with carbon black (Example 2) shows the lower haze number of 2.2. The same effect is observed in a comparison of Example 3 and Comparative Example 5, wherein both meet scale 1.7 (EN 169) requirements, but Example 3 has a significantly lower haze of 1.4 where the combination of $LaB_6$ and CB is used. Comparative Examples 4 and 6, each of which fails its respective EN 169 standard, demonstrate the improvement carbon black conveys in enhancing the effectiveness of a given $LaB_6$ loading in meeting the EN 169 scale 2.5 and 1.7 requirements at lower haze, and allow for the decreased loadings to meet these requirements in Examples 2 and 3, respectively.

Figure 2:
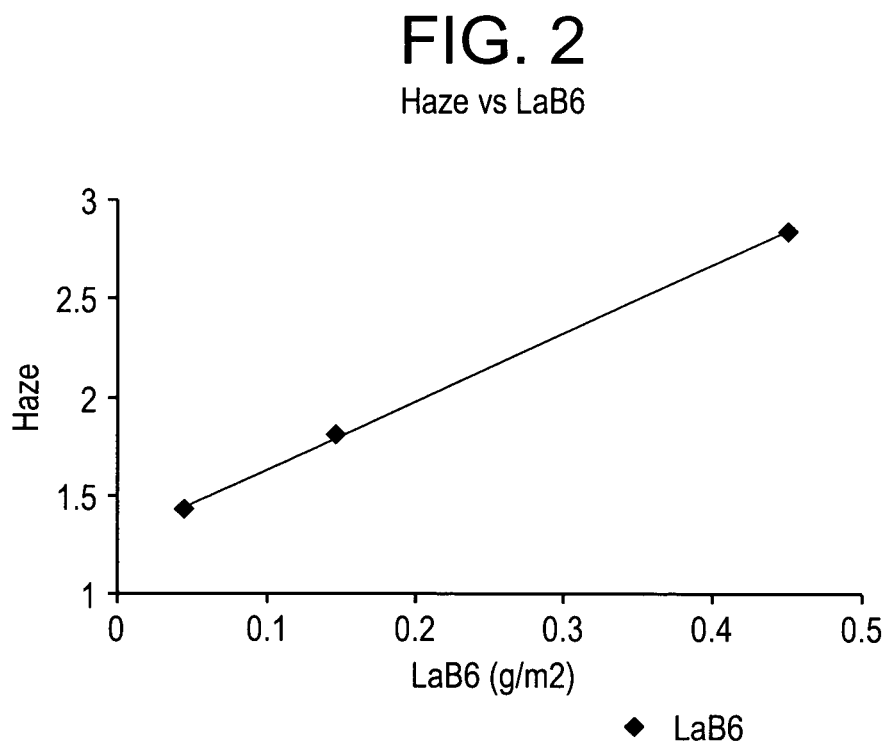

For comparison purposes, FIG. 2 is included to demonstrate the relationship between increasing $LaB_6$ loadings and increasing haze in the compositions, absent added carbon black. It can be assumed that further increases in haze can be extrapolated for $LaB_6$ loadings in excess of 0.45 g/m². The measurement of haze at these excess loadings was not obtained due to limitations of the analytical equipment. However, a qualitative visual comparison of two samples (at 1.0 mm thickness) under illumination with a visible light source, each of which fulfills EN 169 scale 5 requirements, show that the one containing 1.56 g/m² $LaB_6$ diffuses more light, i.e., has higher haze, than the second containing 0.48 g/m² $LaB_6$ and 0.24 g/m² carbon black.

Example 4

Method for determining a suitable loadings of $LaB_6$ and carbon black for the compositions to meet EN 169 and/or EN 171 requirements. A transfer function has been developed to estimate the level of carbon black and $LaB_6$ needed to fulfill specific UV, VIS and IR transmission requirements in EN169 and/or EN171. The transfer functions were derived from a set of experiments as given in Table 4 (1 mm):

The transfer functions (equations) were derived from the above data and were determined using least squares polynomial fits of plots of the above data. The equations are as follows:

$$Log_{10}(\% T_{VIS}) = -1.03 + (-0.64*[LaB_6]) + (-2.28*[CB]) + (0.24*[LaB_6]^2) + (-0.15*[LaB_6]*[CB]);$$ (Equation 1)

$$Log_{10}(\% T_{NIR}(780\text{-}1400 \text{ nm})) = 1.95418 + (-51.52787*[LaB_6]) + (-23.09434*[CB]) + (249.97741*[LaB_6]^2);$$ (Equation 2)

$$Log_{10}(\% T_{NIR}(780\text{-}2000 \text{ nm})) = 1.91554 + (-24.10754*[LaB_6]) + (-19.34173*[CB]) + (161.13859*[LaB_6]^2) + (41.93046*[LaB_6]*[CB]);$$ (Equation 3)

wherein % $T_{VIS}$ is the % transmission in the visible spectrum, % $T_{NIR}$ (780-1400 nm) is the % transmission in the near IR region from 780 to 1400 nanometers, % $T_{NIR}$ (780-2000 nm) is the % transmission in the near IR region from 780 to 2000 nanometers, $[LaB_6]$ is the concentration of $LaB_6$ in g/m², and [CB] is the concentration of carbon black in g/m². The equations can be used to calculate the maximum level of carbon needed for each scale in both norms. Tables 3 and 4 (below) show the maximum amount of carbon black that can be used to achieve values consistent with EN 169 and EN 171. In turn, the amount of $LaB_6$ used to achieve these values can be minimized.

As determined using the above data and equations, the amount of carbon black that can be used is from 0.011 g/m² (e.g., Example 3 in Table 3) to 1.54 g/m² based on a standard carbon black (Monarch™ 800 from Cabot BV). Use of a standard carbon black is recommended as it has been observed that different types of carbon black can have a variation of up to 10% in visible light transmission (% $T_{VIS}$) and up to 100% when other colorants such as dyes are used.

TABLE 4

| Form. No.[f] | $LaB_6$ (g/m²) | C.B. (g/m²) | Avg. % $T_{VIS}$ | Avg. % $T_{NIR}$ at 780-1400 nm | Avg. % $T_{NIR}$ at 780-2000 nm |
|---|---|---|---|---|---|
| 1 | 0.06575 | 0.050 | 0.032 | 0.031 | 1.49 |
| 2 | 0.033625 | 0.050 | 0.098 | 0.25 | 2.66 |
| 3 | 0.06575 | 0.100 | 0.000082 | 0.0018 | 0.17 |
| 4 | 0.0015 | 0.000 | 82.5 | 77.2 | 77.7 |
| 5 | 0.033625 | 0.000 | 25.2 | 3.16 | 19.7 |
| 6 | 0.06575 | 0.000 | 10.0 | 0.37 | 10.4 |
| 7 | 0.0015 | 0.000 | 81.8 | 75.7 | 76.7 |
| 8 | 0.033625 | 0.100 | 0.00021 | 0.012 | 0.25 |
| 9 | 0.0015 | 0.000 | 82.3 | 76.4 | 77.2 |
| 10 | 0.0015 | 0.100 | 0.0080 | 0.43 | 1.07 |
| 11 | 0.06575 | 0.100 | 0.000480035 | 0.0032 | 0.34 |
| 12 | 0.0015 | 0.100 | 0.0052 | 0.30 | 0.80 |
| 13 | 0.05 | 0.040 | 0.13 | 0.14 | 2.74 |
| 14 | 0.06 | 0.030 | 0.27 | 0.11 | 3.31 |
| 15 | 0.04 | 0.030 | 0.76 | 0.45 | 5.51 |
| 16 | 0.05 | 0.020 | 1.06 | 0.31 | 5.65 |
| 17 | 0.04 | 0.020 | 1.71 | 0.65 | 7.25 |
| 18 | 0.025 | 0.015 | 6.29 | 3.06 | 13.8 |
| 19 | 0.03 | 0.010 | 10.2 | 2.64 | 15.2 |
| 20 | 0.02 | 0.005 | 24.4 | 8.04 | 24.4 |
| 21 | 0.01 | 0.005 | 36.0 | 23.1 | 37.6 |
| 22 | 0.005 | 0.001 | 62.8 | 47.2 | 57.3 |
| 23 | 0.005 | 0.000 | 71.5 | 50.6 | 60.6 |

[f]All examples in Table 4 are 1.0 mm in thickness.

Using transfer Equations 1-3, optimum loadings (in g/m$^2$) for carbon black were calculated to meet visor scale standards for EN 169 (Table 5) and EN 171 (Table 6). These values, so calculated using Equations 1-3, are as follows:

TABLE 5

| Scale number EN 169 | LaB$_6$ (g/m$^2$) | CB (g/m$^2$) | % T$_{VIS}$ | Calculated data % T$_{NIR}$ (780-1400 nm) | % T$_{NIR}$ (780-2000 nm) |
|---|---|---|---|---|---|
| 1.2 | 0.0180 | 0.0324 | 74.4 | 65.4 | x |
| 1.4 | 0.0324 | 0.0516 | 58.1 | 52 | x |
| 1.7 | 0.0492 | 0.0768 | 43.2 | 40 | x |
| 2 | 0.0708 | 0.1092 | 29.1 | 28.02 | x |
| 2.5 | 0.1260 | 0.1320 | 17.8 | 15.31 | x |
| 3 | 0.1020 | 0.2376 | 8.5 | 12 | x |
| 4 | 0.1200 | 0.3432 | 3.2 | 6.4 | x |
| 5 | 0.1488 | 0.4404 | 1.2 | 3.2 | x |
| 6 | 0.1668 | 0.5484 | 0.44 | 1.7 | x |
| 7 | 0.2040 | 0.6444 | 0.16 | 0.81 | x |
| 8 | 0.2280 | 0.7428 | 0.061 | 0.43 | x |
| 9 | 0.2784 | 0.8268 | 0.023 | 0.2 | x |
| 10 | 0.3144 | 0.9216 | 0.0085 | 0.1 | x |
| 11 | 0.3552 | 1.0128 | 0.0032 | 0.05 | x |
| 12 | 0.3804 | 1.1112 | 0.0012 | 0.027 | x |
| 13 | 0.4152 | 1.2084 | 0.00044 | 0.014 | x |
| 14 | 0.4596 | 1.3008 | 0.00016 | 0.007 | x |
| 15 | 0.5556 | 1.3656 | 0.000061 | 0.003 | x |
| 16 | 0.4260 | 1.5384 | 0.000023 | 0.003 | x |

TABLE 6

| Scale number EN 171 | LaB$_6$ (g/m$^2$) | CB (g/m$^2$) | % T$_{VIS}$ | Calculated data % T$_{NIR}$ (780-1400 nm) | % T$_{NIR}$ (780-2000 nm) |
|---|---|---|---|---|---|
| 4-3 | 0.432 | 0.0756 | 8.5 | 1.9 | 14 |
| 4-4 | 0.4248 | 0.1884 | 3.2 | 1.2 | 9.6 |
| 4-5 | 0.4308 | 0.2988 | 1.2 | 0.71 | 6.5 |
| 4-6 | 0.4296 | 0.4128 | 0.44 | 0.43 | 4.4 |
| 4-7 | 0.4548 | 0.5196 | 0.16 | 0.23 | 2.9 |
| 4-8 | 0.4572 | 0.6276 | 0.061 | 0.14 | 2.01 |
| 4-9 | 0.4872 | 0.726 | 0.023 | 0.075 | 1.36 |
| 4-10 | 0.4656 | 0.8472 | 0.0085 | 0.05 | 0.936 |

Using the values shown in Tables 5 and 6, optimum loadings of LaB$_6$ and carbon black can be determined which meet the requirements for any of the scale number for EN 169 and/or EN 171. These optimized loadings are useful to ensure the lowest possible haze values for a composition that meets the requirements for a particular scale.

The singular forms "a," "an," and "the" include plural referents unless the context clearly dictates otherwise. The endpoints of all ranges reciting the same characteristic are combinable and inclusive of the recited endpoint. All references are incorporated herein by reference.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

We claim:

1. A composition comprising:
    about 70 to about 99.9 percent by weight of a polycarbonate resin,
    about 0.000075 to about 1 percent by weight of an inorganic infrared shielding additive comprising a metal boride, metal tungsten oxide, or combination thereof, and
    about 0.0001 to about 2.7 percent by weight carbon black,
    wherein the weight ratio of inorganic infrared shielding additive to carbon black is about 0.001:1 to about 70:1,
    wherein all percents by weight are based on the total weight of the composition,
    wherein the composition has inorganic infrared shielding additive present at about 0.01 to about 1.0 grams per square meter, carbon black present at about 0.001 to about 2.0 grams per square meter, and a haze of less than about 5% as measured at a thickness when molded of about 2.5 mm according to ASTM D 1003-00, and
    the composition has a melt volume rate of about 1 to about 8 grams per 10 minutes flow as determined at 300° C. and 1.2 Kg according to ISO 1133,
    and further wherein the respective amounts of inorganic infrared shielding additive and carbon black are effective to meet the requirements for at least one scale of European Norm EN 169 and EN 171, while providing lower haze or lower melt volume rate or both lower haze and lower melt volume rate than the composition would exhibit if it utilized the inorganic infrared shielding additive as its only infrared absorber in an amount sufficient to meet said at least one scale of European Norm EN 169and/or EN 171.

2. The composition of claim 1 wherein the polycarbonate resin comprises bisphenol-A polycarbonate.

3. The composition of claim 1 wherein the inorganic infrared shielding additive is selected from LaB$_6$, NdB$_6$, PrB$_6$, CeB$_6$, GdB$_6$, TbB$_6$, DyB$_6$, HoB$_6$, YB$_6$, SmB$_6$, EuB$_6$, LaB$_6$, TmB$_6$, YbB$_6$, LuB$_6$, SrB$_6$, TiB$_2$, ZrB$_2$, HfB$_2$, VB$_2$, TaB$_2$, CrB, CrB$_2$, MoB$_2$, Mo$_2$B$_5$, MoB, W$_2$B$_5$, K(WO$_3$)$_3$, Rb(WO$_3$)$_3$, Cs(WO$_3$)$_3$, Tl(WO$_3$)$_3$ or a combination comprising at least one of the foregoing inorganic infrared shielding additives.

4. The composition of claim 1, wherein the ratio of inorganic infrared shielding additive to carbon black is from 0.2769 to 5.7143.

5. The article of claim 4, wherein the inorganic infrared shielding additive comprises LaB$_6$.

6. The article of claim 1, wherein the inorganic infrared shielding additive comprises LaB$_6$.

7. An article comprising the composition of claim 1.

8. The article of claim 7 wherein the article is protective eyewear.

9. The article of claim 7, wherein the carbon black is present in an amount of 0.011 to 1.54 g/m$^2$.

10. The article of claim 7, wherein the ratio of inorganic infrared shielding additive to carbon black is from 0.2769 to 5.7143.

11. The article of claim 10, wherein the inorganic infrared shielding additive comprises LaB$_6$.

12. An article comprising a layer of a composition, wherein the composition comprises:
    about 70 to about 99.9 percent by weight of a polycarbonate resin,
    about 0.000075 to about 1 percent by weight of an inorganic infrared shielding additive comprising a metal boride, metal tungsten oxide, or combination thereof, and
    about 0.0001 to about 2.7 percent by weight carbon black,
    wherein all percents by weight are based on the total weight of the composition,
    wherein the weight ratio of inorganic infrared shielding additive to carbon black is about 0.001:1 to about 70:1, wherein the layer has the inorganic infrared shielding additive present at about 0.01 to about 1.0 grams per square meter and has the carbon black present at about 0.001 to about 2.0 grams per square meter, has a haze of less than about 5% as measured at a thickness of about 2.5 mm according to ASTM D1003-00, and the composition has a melt volume rate of about 1 to about 8 grams per 10 minutes flow as determined at 300° C. and 1.2 Kg according to ISO 1133, and further wherein the respective amounts of inorganic infrared shielding additive and carbon black are effective to meet the requirements for at least one scale of European Norm EN 169 and/or EN 171, while providing lower haze or lower melt volume rate or both lower haze and lower melt volume rate than the composition would exhibit if it utilized the inorganic infrared shielding additive as its only infrared absorber in an amount sufficient to meet said at least one scale of European Norm EN 169 and/or EN 171.

13. An article comprising a composition, wherein the composition comprises:
about 70 to about 99.9 percent by weight of a polycarbonate resin,
about 0.000075 to about 1 percent by weight of an inorganic infrared shielding additive comprising a metal boride, metal tungsten oxide, or combination thereof, and
about 0.0001 to about 2.7 percent by weight carbon black,
wherein all percents by weight are based on the total weight of the composition,
wherein the weight ratio of inorganic infrared shielding additive to carbon black is about 0.001:1 to about 70:1,
wherein the article prepared from the composition has a haze of less than about 5% as measured at a thickness of about 2.5 mm according to ASTM D1003-00, and
the composition has a melt volume rate of about 1 to about 8 grams per 10 minutes flow as determined at 300° C. and 1.2 Kg according to ISO 1133
and further wherein the respective amounts of inorganic infrared shielding additive and carbon black are effective to meet the requirements for at least one scale of European Norm EN 169 and/or EN 171, while providing lower haze or lower melt volume rate or both lower haze and lower melt volume rate than the composition would exhibit if it utilized the inorganic infrared shielding additive as its only infrared absorber in an amount sufficient to meet said at least one scale of European Norm EN 169 and/or EN 171.

14. The article of claim 13, wherein the carbon black is present in an amount of 0.011 to 1.54 g/m².

15. The article of claim 13, wherein the ratio of inorganic infrared shielding additive to carbon black is from 0.2769 to 5.7143.

16. The article of claim 15, wherein the inorganic infrared shielding additive comprises $LaB_6$.

17. A masterbatch comprising:
a carrier resin comprising a polycarbonate resin, and
an infrared shielding additive package, comprising:
an inorganic infrared shielding additive comprising a metal boride, metal tungsten oxide, or combination thereof, and
carbon black,
wherein the weight ratio of inorganic infrared shielding additive to carbon black in the infrared shielding additive package is about 0.001:1 to about 70:1, and wherein the infrared shielding additive package is present in the masterbatch in an amount of about 0.0001 to about 20 wt % of the combined weights of the carrier resin and infrared shielding additive package,
wherein the masterbatch, when combined with a base resin in an amount of about 5 to about 20 wt % based on the combined weight of the masterbatch and the base resin, and having inorganic infrared shielding additive present at about 0.01 to about 1.0 grams per square meter, and carbon black present at about 0.001 to about 2.0 grams per square meter, has a haze of less than about 5% as measured at a thickness when molded of about 2.5 mm according to ASTM D1003-00, and
the composition has a melt volume rate of about 1 to about 8 grams per 10 minutes flow as determined at 300° C and 1.2 Kg according to ISO 1133
and further wherein the respective amounts of inorganic infrared shielding additive and carbon black are effective to meet the requirements for at least one scale of European Norm EN 169 and/or EN 171, while providing lower haze or lower melt volume rate or both lower haze and lower melt volume rate than the composition would exhibit if it utilized the inorganic infrared shielding additive as its only infrared absorber in an amount sufficient to meet said at least one scale of European Norm EN 169 and/or EN 171.

18. The masterbatch of claim 17 wherein the inorganic infrared shielding additive is selected from $LaB_6$, $NdB_6$, $PrB_6$, $CeB_6$, $GdB_6$, $TbB_6$, $DyB_6$, $HoB_6$, $YB_6$, $SmB_6$, $EuB_6$, $LaB_6$, $TmB_6$, $YbB_6$, $LuB_6$, $SrB_6$, $TiB_2$, $ZrB_2$, $HfB_2$, $VB_2$, $TaB_2$, $CrB$, $CrB_2$, $MoB_2$, $Mo_2B_5$, $MoB$, $W_2B_5$, $K(WO_3)_3$, $Rb(WO_3)_3$, $Cs(WO_3)_3$, $Tl(WO_3)_3$, or a combination comprising at least one of the foregoing inorganic infrared shielding additives.

19. A composition comprising the masterbatch of claim 17.

* * * * *